US009046767B2

(12) United States Patent
Aqad et al.

(10) Patent No.: US 9,046,767 B2
(45) Date of Patent: Jun. 2, 2015

(54) PHOTOACID GENERATOR, PHOTORESIST, COATED SUBSTRATE, AND METHOD OF FORMING AN ELECTRONIC DEVICE

(71) Applicant: ROHM AND HAAS ELECTRONIC MATERIALS LLC, Marlborough, MA (US)

(72) Inventors: Emad Aqad, Northborough, MA (US); Irvinder Kaur, Northborough, MA (US); Cong Liu, Shrewsbury, MA (US); Mingqi Li, Shrewsbury, MA (US); Cheng-Bai Xu, Southborough, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 19 days.

(21) Appl. No.: 14/063,148

(22) Filed: Oct. 25, 2013

(65) Prior Publication Data

US 2015/0118618 A1    Apr. 30, 2015

(51) Int. Cl.
| G03F 7/004 | (2006.01) |
| G03F 7/028 | (2006.01) |
| C07C 381/12 | (2006.01) |
| C07D 319/04 | (2006.01) |
| C07D 319/08 | (2006.01) |
| G03F 7/027 | (2006.01) |

(52) U.S. Cl.
CPC .............. *G03F 7/027* (2013.01); *C07C 381/12* (2013.01); *C07D 319/04* (2013.01); *C07D 319/08* (2013.01)

(58) Field of Classification Search
CPC .. C07D 319/04; C07D 319/08; C07C 381/12; G03F 7/004; G03F 7/028; G03F 7/20
USPC ........ 549/200; 430/270.1, 921, 923, 924, 322
See application file for complete search history.

(56) References Cited

U.S. PATENT DOCUMENTS

| 5,128,232 | A | 7/1992 | Thackeray et al. |
| 5,279,921 | A | 1/1994 | Onishi et al. |
| 7,301,047 | B2 | 11/2007 | Yoshida et al. |
| 7,304,175 | B2 | 12/2007 | Harada et al. |
| 7,459,260 | B2 | 12/2008 | Chandhok et al. |
| 7,488,568 | B2 | 2/2009 | Iwai et al. |
| 7,615,330 | B2 | 11/2009 | Kamimura et al. |
| 7,718,344 | B2 | 5/2010 | Kamimura et al. |
| 7,776,510 | B2 | 8/2010 | Iwai et al. |
| 8,227,624 | B2 | 7/2012 | Nakayashiki et al. |
| 8,318,403 | B2 | 11/2012 | Ichikawa et al. |
| 8,354,217 | B2 | 1/2013 | Ichikawa et al. |
| 8,367,298 | B2 | 2/2013 | Ichikawa et al. |
| 8,415,082 | B2 | 4/2013 | Utsumi et al. |
| 8,420,294 | B2 | 4/2013 | Ichikawa et al. |
| 8,507,575 | B2 | 8/2013 | Matsumura et al. |
| 2010/0239978 | A1* | 9/2010 | Wada et al. ................ 430/270.1 |
| 2010/0248149 | A1 | 9/2010 | Tsuchimura et al. |
| 2010/0316951 | A1* | 12/2010 | Ichikawa et al. .......... 430/270.1 |
| 2012/0136155 | A1 | 5/2012 | Makabe et al. |
| 2013/0344438 | A1 | 12/2013 | Aqad et al. |

FOREIGN PATENT DOCUMENTS

| CN | 102289149 A | 12/2011 |
| EP | 0164248 A2 | 12/1985 |
| EP | 0783136 A2 | 7/1997 |
| EP | 0829766 A2 | 3/1998 |
| JP | 2011201860 A | 10/2011 |
| JP | 2011201866 A | 10/2011 |
| JP | 2011256390 A | 12/2011 |
| JP | 2014105166 A | 6/2014 |
| WO | 2011162408 A1 | 12/2011 |

OTHER PUBLICATIONS

Xiw W,. Tanabe G., Akaki J, Morikawa T., Ninomiya K., Minematsu T., Yoshikawa M., Wu X., Muraoka O.—Isolation, structure identification and SAR studies on thiosugar sulfonium salts, neosalaprinol and neoponkoranol, as potent alpha-glucosidase inhibitors, Bioorganic & Medicinal Chemistry 19 (2011), pp. 2015-2022.*
Non-Final Office Action dated Nov. 20, 2014; U.S. Appl. No. 13/925,926, filed Jun. 25, 2013.
U.S. Appl. No. 13/854,078, filed Mar. 30, 2013, "Acid Generators and Photoresists Comprising the Same"; 35 Pages.
U.S. Appl. No. 14/012,577, filed Aug. 28, 2013, "Photoacid Generator, Photoresist, Coated Substrate, and Method of Forming an Electronic Device", 31 Pages.
Non-Final Office Action dated Dec. 22, 2014; U.S. Appl. No. 14/012,577, filed Aug. 28, 2013.

* cited by examiner

*Primary Examiner* — Anca Eoff
(74) *Attorney, Agent, or Firm* — Cantor Colburn LLP

(57) ABSTRACT

A photoacid generator compound has the formula (1)

(1)

[structural chemical formula]

wherein a, b, c, d, e, x, $L^1$, $L^2$, $L^3$, $L^4$, $R^1$, $R^2$, X, and $Z^-$ are defined herein. The photoacid generator compound exhibits good solubility in solvents typically used to formulate photoresist compositions and negative tone developers. Described herein are a photoresist composition including the photoacid generator compound, a coated substrate including the photoresist composition, and a device-forming method utilizing the photoresist composition.

19 Claims, 1 Drawing Sheet

PHOTOACID GENERATOR, PHOTORESIST, COATED SUBSTRATE, AND METHOD OF FORMING AN ELECTRONIC DEVICE

FIELD

The present invention relates to photoacid generators and their use in photoresist compositions.

INTRODUCTION

Advanced lithographic techniques such as 193 nanometer immersion lithography have been developed to achieve high quality and smaller feature sizes in microlithography processes, for purposes of forming ever-smaller logic and memory transistors. It is important to achieve both smaller critical dimension (CD) in the imaged photoresist used in the microlithography process, and for the photoresists to provide improved line width roughness (LWR) or contact hole dimension uniformity, while still retaining good process control tolerances such as high exposure latitude (EL). Also important is low mask error factor (MEF), which is defined as the ratio of critical dimension (CD) change on the resolved resist pattern to the dimension change on the mask pattern.

Photoacid generators are used to generate protons in response to irradiation. The cations of onium salt-based photoacid generators are typically highly hydrophobic, a property that renders the photoacid generators poorly soluble in negative tone developers, such as n-butyl acetate, 2-heptanone, n-butyl propionate or blends made of the aforementioned solvents. The use of such photoacid generators in photoresists for Positive Tone Development (PTD) lithography is disadvantageous due to low post-exposure stability of the latent image, which causes deterioration of the photoresist pattern. Furthermore, the use of such hydrophobic onium salts lead to a suppression of the photoresist dissolution in alkaline developing solutions. There is a need for photoacid generators that are highly soluble in negative tone developers and rendered poorly soluble upon exposure and post-exposure bake treatment. Such photoacid generators would also be advantageous for the formulation of photoresists for Negative Tone Development (NTD) lithography since these solubility characteristics are important for achieving improved Critical Dimension Uniformity.

SUMMARY

One embodiment is a photoacid generator compound having formula (1)

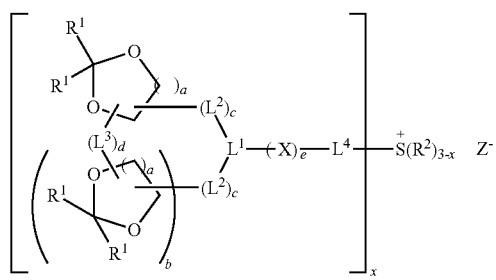

(1)

wherein a is independently at each occurrence 0, 1, 2, 3, 4, 5, 6, 7, 8, 9, 10, 11, or 12; b is independently at each occurrence 0, 1, 2, 3, 4, or 5; c is independently at each occurrence 0 or 1; d and e are each independently 0 or 1; x is 1, 2, or 3; $L^1$ and $L^3$ are each independently at each occurrence a single bond, an unsubstituted or substituted $C_{1-20}$ aliphatic group, an unsubstituted or substituted $C_{6-20}$ aromatic group, or an unsubstituted or substituted $C_{3-20}$ heteroaromatic group; wherein $L^1$ and $L^3$ are optionally directly covalently linked; and wherein one or more of $L^1$ and $L^3$ are optionally substituted with a polymerizable group; $L^2$ is independently at each occurrence a single bond, a carbonyl group, an ester group, an amide group, an ether oxygen, or a $C_{1-20}$ aliphatic group optionally substituted with an ether oxygen, a carbonyl group, an ester group, an ether oxygen, or a combination thereof, wherein two occurrences of $L^2$ are optionally directly covalently linked; and wherein one or more occurrences of $L^2$ are optionally substituted with a polymerizable group; $L^4$ is independently at each occurrence an unsubstituted or substituted $C_{6-20}$ arylene, an unsubstituted or substituted $C_{3-20}$ heteroarylene, an unsubstituted or substituted $C_{1-20}$ linear or branched alkylene, or an unsubstituted or substituted $C_{3-20}$ cycloalkylene; wherein $L^4$ is optionally covalently linked to an occurrence of $R^2$; and wherein one or more occurrences of $L^4$ are optionally substituted with a polymerizable group; $R^1$ is independently at each occurrence hydrogen, an unsubstituted or substituted $C_{1-30}$ linear or branched alkyl, an unsubstituted or substituted $C_{3-30}$ cycloalkyl, an unsubstituted or substituted $C_{6-30}$ aryl, or an unsubstituted or substituted $C_{3-30}$ heteroaryl; wherein each occurrence of $R^1$ is optionally covalently linked to an adjacent occurrence of $R^1$; and wherein one or more occurrences of $R^1$ are optionally substituted with a polymerizable group; $R^2$ is independently at each occurrence an unsubstituted or substituted $C_{6-40}$ aryl, an unsubstituted or substituted $C_{3-40}$ heteroaryl, an unsubstituted or substituted $C_{1-40}$ alkyl, or an unsubstituted or substituted $C_{3-40}$ cycloalkyl; wherein when x is 1, the two groups $R^2$ are optionally directly covalently linked to each other; and wherein one or more occurrences of $R^2$ are optionally substituted with a polymerizable group; X is independently at each occurrence an —O—, —S—, or an ether-, carbonyl-, ester-, carbonate-, amine-, amide-, urea-, sulfate-, sulfonate-, or sulfonamide-containing group, or combination thereof; wherein one or more occurrences of X are optionally substituted with a polymerizable group; and $Z^-$ is an organic anion; wherein $Z^-$ is optionally substituted with a polymerizable group.

Another embodiment is a polymer comprising a unit formed from the photoacid generator compound.

Another embodiment is a photoresist composition comprising the polymer comprising a unit formed from the photoacid generator compound, and an acid-sensitive polymer, wherein the polymer comprising a unit formed from the photoacid generator compound, and the acid-sensitive polymer are the same or different.

Another embodiment is a photoresist composition comprising: an acid-sensitive polymer, and the photoacid generator compound.

Another embodiment is a coated substrate comprising: (a) a substrate having one or more layers to be patterned on a surface thereof; and (b) a layer of the photoresist composition over the one or more layers to be patterned.

Another embodiment is a method of forming an electronic device, comprising: (a) applying a layer of the photoresist composition on a substrate; (b) pattern-wise exposing the photoresist composition layer to activating radiation; and (c) developing the exposed photoresist composition layer to provide a resist relief image.

These and other embodiments are described in detail below.

DETAILED DESCRIPTION

Figure 1:
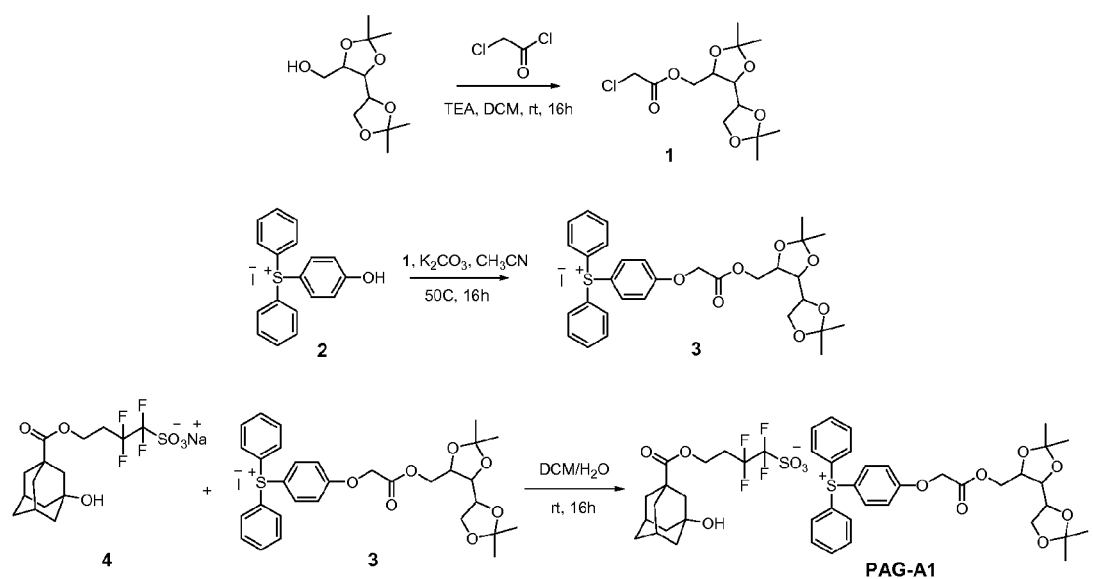
FIG. 1 is a synthetic scheme illustrating the synthesis of the photoacid generator PAG-A1.

The present inventors have determined that photoacid generators having ketal-substituted sulfonium ions exhibit improved Exposure Latitude (EL) and Mask Error Factor (MEF) relative to triphenylsulfonium perfluoroalkylsulfonates in positive tone development, and improved Critical Dimension Uniformity (CDU) relative to triphenylsulfonium 3-hydroxyadamant-1-ylmethyl 2,2-difluoro-2-sulfonatoacetate in negative tone development.

Thus, one embodiment is a photoacid generator compound having formula (1)

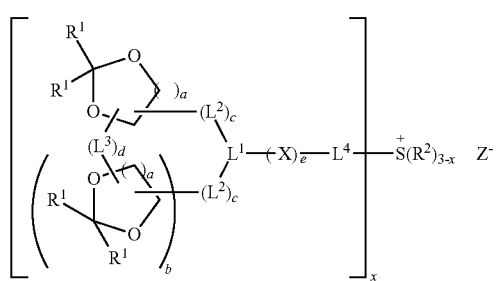

wherein a is independently at each occurrence 0, 1, 2, 3, 4, 5, 6, 7, 8, 9, 10, 11, or 12; b is independently at each occurrence 0, 1, 2, 3, 4, or 5; c is independently at each occurrence 0 or 1; d and e are each independently 0 or 1; x is 1, 2, or 3; $L^1$ and $L^3$ are each independently at each occurrence a single bond, an unsubstituted or substituted $C_{1-20}$ aliphatic group, an unsubstituted or substituted $C_{6-20}$ aromatic group, or an unsubstituted or substituted $C_{3-20}$ heteroaromatic group; wherein $L^1$ and $L^3$ are optionally directly covalently linked; and wherein one or more of $L^1$ and $L^3$ are optionally substituted with a polymerizable group; $L^2$ is independently at each occurrence a single bond, a carbonyl group, an ester group, an amide group, an ether oxygen, or a $C_{1-20}$ aliphatic group optionally substituted with an ether oxygen, a carbonyl group, an ester group, an ether oxygen, or a combination thereof, wherein two occurrences of $L^2$ are optionally directly covalently linked; and wherein one or more occurrences of $L^2$ are optionally substituted with a polymerizable group; $L^4$ is independently at each occurrence an unsubstituted or substituted $C_{6-20}$ arylene, an unsubstituted or substituted $C_{3-20}$ heteroarylene, an unsubstituted or substituted $C_{1-20}$ linear or branched alkylene, or an unsubstituted or substituted $C_{3-20}$ cycloalkylene; wherein $L^4$ is optionally covalently linked to an occurrence of $R^2$; and wherein one or more occurrences of $L^4$ are optionally substituted with a polymerizable group; $R^1$ is independently at each occurrence hydrogen, an unsubstituted or substituted $C_{1-30}$ linear or branched alkyl, an unsubstituted or substituted $C_{3-30}$ cycloalkyl, an unsubstituted or substituted $C_{6-30}$ aryl, or an unsubstituted or substituted $C_{3-30}$ heteroaryl; wherein each occurrence of $R^1$ is optionally covalently linked to an adjacent occurrence of $R^1$; and wherein one or more occurrences of $R^1$ are optionally substituted with a polymerizable group; $R^2$ is independently at each occurrence an unsubstituted or substituted $C_{6-40}$ aryl, an unsubstituted or substituted $C_{3-40}$ heteroaryl, an unsubstituted or substituted $C_{1-40}$ alkyl, or an unsubstituted or substituted $C_{3-40}$ cycloalkyl; wherein when x is 1, the two groups $R^2$ are optionally directly covalently linked to each other; and wherein one or more occurrences of $R^2$ are optionally substituted with a polymerizable group; X is independently at each occurrence an —O—, —S—, or an ether-, carbonyl-, ester-, carbonate-, amine-, amide-, urea-, sulfate-, sulfonate-, or sulfonamide-containing group, or combination thereof; wherein one or more occurrences of X are optionally substituted with a polymerizable group; and $Z^-$ is an organic anion; wherein $Z^-$ is optionally substituted with a polymerizable group.

As used herein, the term "ketal" shall be understood to be generic to "acetal" and "ketal". "Substituted" shall be understood to mean including at least one substituent such as a halogen (i.e., F, Cl, Br, I), hydroxyl, amino, thiol, carboxyl, carboxylate, ester (including acrylates, methacrylates, and lactones), amide, nitrile, sulfide, disulfide, nitro, $C_{1-18}$ alkyl, $C_{1-18}$ alkenyl (including norbornenyl), $C_{1-18}$ alkoxyl, $C_{2-18}$ alkenoxyl (including vinyl ether), $C_{6-18}$ aryl, $C_{6-18}$ aryloxyl, $C_{7-18}$ alkylaryl, or $C_{7-18}$ alkylaryloxyl. "Fluorinated" shall be understood to mean having one or more fluorine atoms incorporated into the group. For example, where a $C_{1-18}$ fluoroalkyl group is indicated, the fluoroalkyl group can include one or more fluorine atoms, for example, a single fluorine atom, two fluorine atoms (e.g., as a 1,1-difluoroethyl group), three fluorine atoms (e.g., as a 2,2,2-trifluoroethyl group), or fluorine atoms at each free valence of carbon (e.g., as a perfluorinated group such as —$CF_3$, —$C_2F_5$, —$C_3F_7$, or —$C_4F_9$).

In the formula (1) structure, the variable "a" determines the size of each ketal-containing ring and is independently at each occurrence 0, 1, 2, 3, 4, 5, 6, 7, 8, 9, 10, 11, or 12. In some embodiments "a" is independently at each occurrence 1 or 2. In some embodiments, "a" is 1 at each occurrence. The variable "b" determines the number of ketal-containing rings in the photoacid generator, that number being x×(b+1). The variable "b" can be 0, 1, 2, 3, 4, or 5. In some embodiments "b" is 0 or 1. In some embodiments, "b" is 1. The variable "c" has two occurrences in formula (1), and it determines the presence or absence of each of two $L^2$ groups. The variable "c" is independently at each occurrence 0 or 1. The variable "d" determines the presence or absence of the $L^3$ group; "d" can be zero or 1. In some embodiments, "d" is 1. The variable "e" determines the presence or absence of the X group; "e" can be zero or 1. In some embodiments, "e" is 1. The variable "x" determines the number of ketal-substituted groups bound to the sulfonium sulfur atom; "x" can be 1, 2, or 3. In some embodiments, x is 1.

In the formula (1) structure, $L^1$ and $L^3$ are each independently at each occurrence a single bond, an unsubstituted or substituted (e.g., with a lactone) $C_{1-20}$ aliphatic group, an unsubstituted or substituted $C_{6-20}$ aromatic group, or an unsubstituted or substituted $C_{3-20}$ heteroaromatic group; wherein $L^1$ and $L^3$ are optionally directly covalently linked (i.e., joined by a covalent linkage that does not include a ketal-containing ring); and wherein one or more of $L^1$ and $L^3$ are optionally substituted with a polymerizable group. Specific examples of $L^1$ include

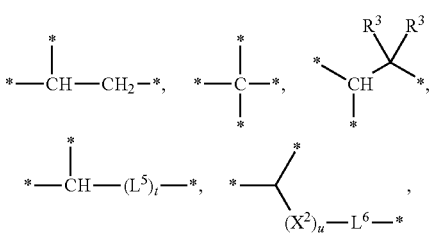

wherein $R^3$ is independently at each occurrence hydrogen, an unsubstituted or substituted $C_{1-30}$ linear or branched alkyl, an unsubstituted or substituted $C_{3-30}$ cycloalkyl, an unsubstituted or substituted $C_{6-30}$ aryl, or an unsubstituted or substituted $C_{3-30}$ heteroaryl, wherein each occurrence of $R^3$ is optionally covalently linked to an adjacent occurrence of $R^3$; t and u are each independently 0 or 1; $L^5$ and $L^6$ are each independently an unsubstituted or substituted $C_{1-20}$ linear or branched alkylene, an unsubstituted or substituted $C_{3-20}$ cycloalkylene, or an unsubstituted or substituted $C_{6-20}$ arylene; and $X^2$ is —O— or —N(R)—, wherein R is hydrogen or $C_{1-6}$ alkyl. Specific examples of $L^3$ include a single bond and —CH$_2$—.

Each occurrence of $L^2$ in formula (1) is independently a single bond, a carbonyl group, an ester group, an amide group, an ether oxygen, or a $C_{1-20}$ aliphatic group optionally substituted with an ether oxygen, a carbonyl group, an ester group, an ether oxygen, or a combination thereof; wherein two occurrences of $L^2$ are optionally directly covalently linked (that is, not linked via $L^1$ or a ketal-containing ring). One or more occurrences of $L^2$ are optionally substituted with a polymerizable group. Specific examples of $L^2$ include

—CH$_2$—, —O—, —CH$_2$—O—C(O)—,

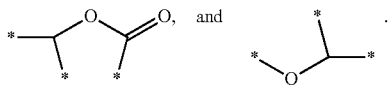

In formula (1), $L^4$ is independently at each occurrence an unsubstituted or substituted $C_{6-20}$ arylene, an unsubstituted or substituted $C_{3-20}$ heteroarylene, an unsubstituted or substituted $C_{1-20}$ linear or branched alkylene, or an unsubstituted or substituted $C_{3-20}$ cycloalkylene. In some embodiments, one or more occurrences of $L^4$ are substituted with a polymerizable group. In some embodiments, $L^4$ is an unsubstituted or substituted $C_{6-20}$ arylene. Specific examples of $L^4$ include 1,3-phenylene, 1,4-phenylene, 1,3-napthalene-diyl, 1,4-napthalene-diyl, 1,5-napthalene-diyl, 1,8-napthalene-diyl, 1,5-pyridine-diyl, 1,4-thiophene-diyl, methylene (—CH$_2$—), dimethylene (—(CH$_2$)$_2$—), 1,4-cyclohexanediyl, and 4,5-norbornenediyl. In some embodiments $L^4$ is 1,4-phenylene.

In formula (1), $R^1$ is independently at each occurrence hydrogen, an unsubstituted or substituted $C_{1-30}$ linear or branched alkyl, an unsubstituted or substituted $C_{3-30}$ cycloalkyl, an unsubstituted or substituted $C_{6-30}$ aryl, or an unsubstituted or substituted $C_{3-30}$ heteroaryl. Specific examples of $R^1$ include methyl and ethyl. In some embodiments $R^1$ is methyl. Each occurrence of $R^1$ is optionally covalently linked to an adjacent occurrence of $R^1$. For example, adjacent occurrences of $R^1$ can combine to form tetramethylene (—(CH$_2$)$_4$—) or pentamethylene (—(CH$_2$)$_5$—). Alternatively, adjacent occurrences of $R^1$ and the carbon to which they are bound can combine to form cyclic groups such 2,2-norbornanediyl, 7,7-norbornanediyl, and 2,2-adamantanediyl. In some embodiments, one or more occurrences of $R^1$ are substituted with a polymerizable group.

$R^2$ in formula (1) is independently at each occurrence an unsubstituted or substituted $C_{6-40}$ aryl, an unsubstituted or substituted $C_{3-40}$ heteroaryl, an unsubstituted or substituted $C_{1-40}$ alkyl, or an unsubstituted or substituted $C_{3-40}$ cycloalkyl. In some embodiments, one or more occurrences of $R^2$ are optionally substituted with a polymerizable group. Specific examples of $R^2$ include phenyl, methylphenyl, t-butylphenyl, fluorophenyl, hydroxyphenyl, biphenyl, naphthyl, 2-pyridinyl, 3-pyridinyl, methyl, tert-butyl, cyclopentyl, and cyclohexyl. When x is 1, the two groups $R^2$ are optionally directly covalently linked to each other. For example, the two $R^2$ groups combined can have one of the structures below, where bonds extending through the single bracket represent bonds to the sulfonium sulfur ion

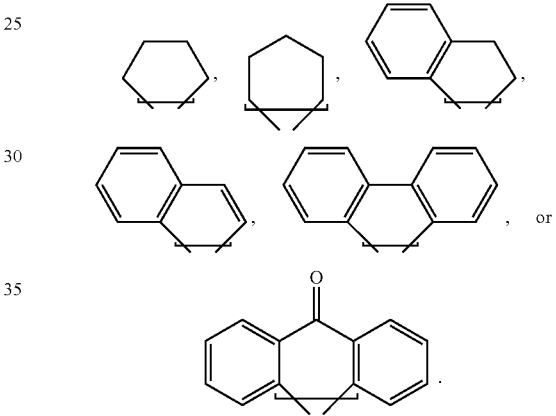

In formula (1), X is independently at each occurrence an —O—, —S—, or an ether-, carbonyl-, ester-, carbonate-, amine-, amide-, urea-, sulfate-, sulfonate-, or sulfonamide-containing group, or combination thereof, wherein one or more occurrences of X are optionally substituted with a polymerizable group. Specific examples of X include —O—, —S—, —C(O)—, —O—C(O)—, —O—C(O)—O—, —C(O)—CH$_2$—, —O—C(O)—CH$_2$—, —O—C(O)—CH$_2$—O—, —O—C(O)—CH$_2$—O—, —N(R)—, —CH$_2$—N(R)—, —CH$_2$—N(R)—C(O)—, —CH$_2$—C(O)—N(R)—, —N(R)—C(O)—N(R)—, —CH$_2$—N(R)—C(O)—N(R)—, —S(O)$_2$—O—, —CH$_2$—S(O)$_2$—O—, —O—S(O)$_2$—O—, —CH$_2$—O—S(O)$_2$—O—, —N(R)S(O)$_2$—, or —CH$_2$—N(R)S(O)$_2$—, wherein R is hydrogen or $C_{1-6}$ alkyl. In some embodiments, X is —O—C(O)—CH$_2$—O—. In other embodiments, one or more occurrences of X are optionally substituted with a polymerizable group.

$Z^-$ in formula (1) is an organic anion comprising an anionic group that can be carboxylate, sulfate, sulfonate, sulfamate, sulfonamidate (anion of sulfonamide), or sulfonimidate (anion of sulfonimide). In some embodiments, $Z^-$ comprises a sulfonate or sulfonimidate group. Specific examples of $Z^-$ include $CF_3(CF_2)_3SO_3^-$

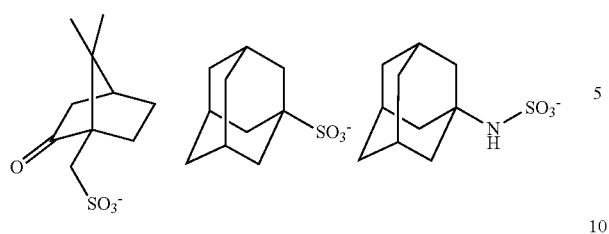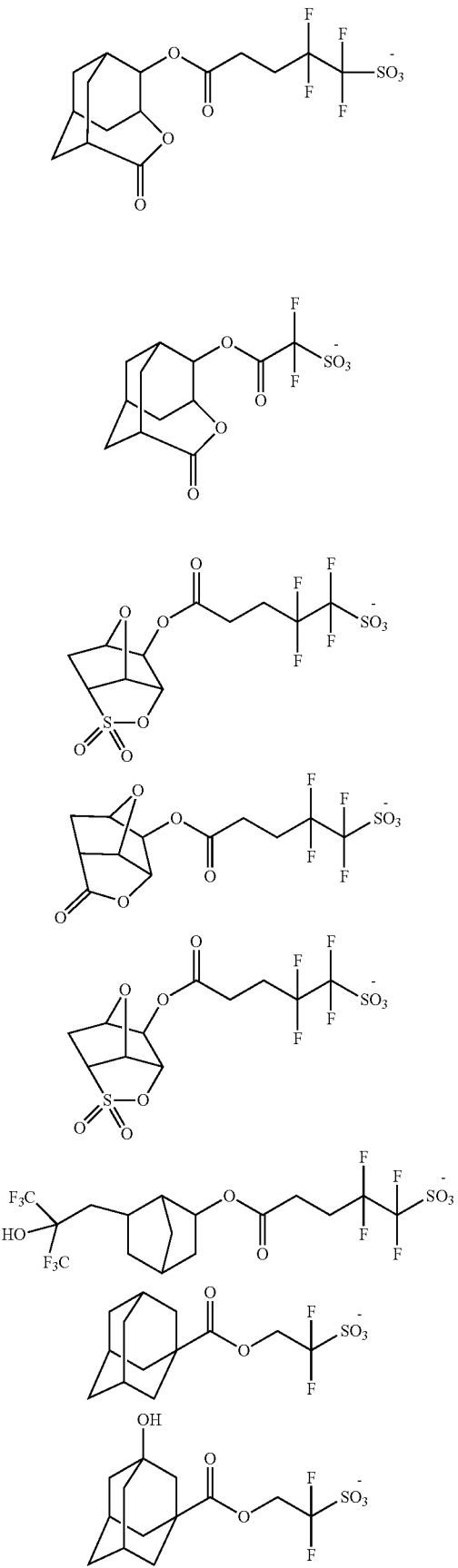

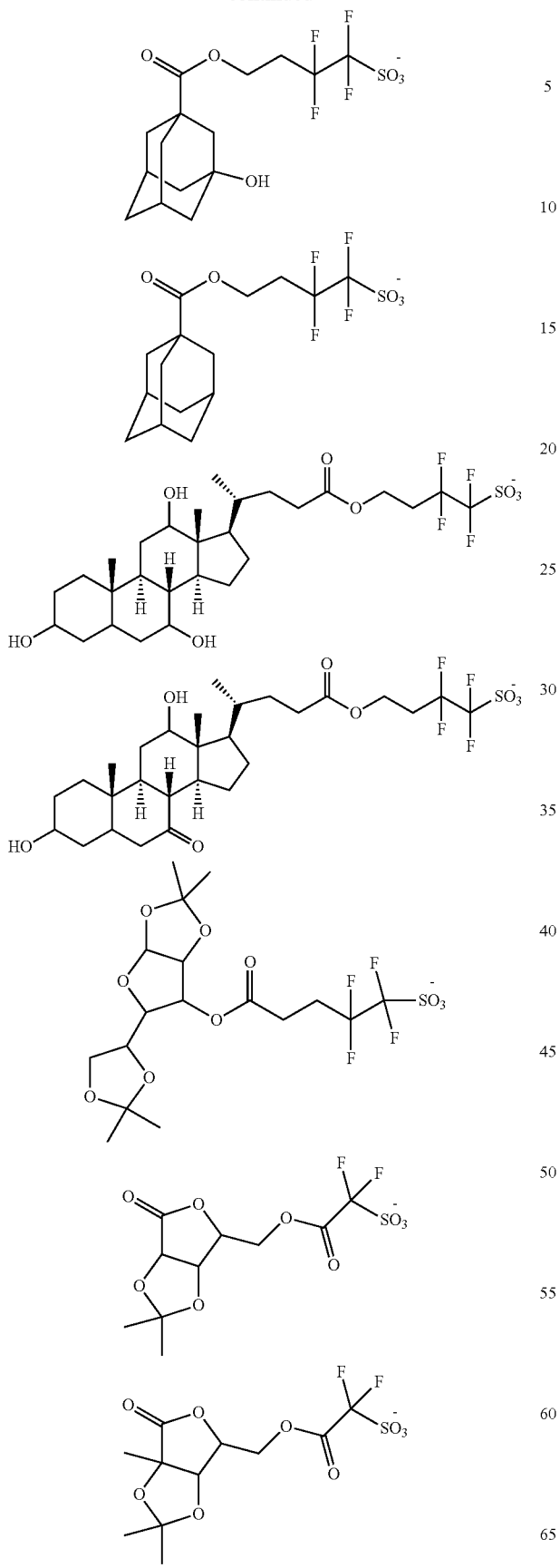
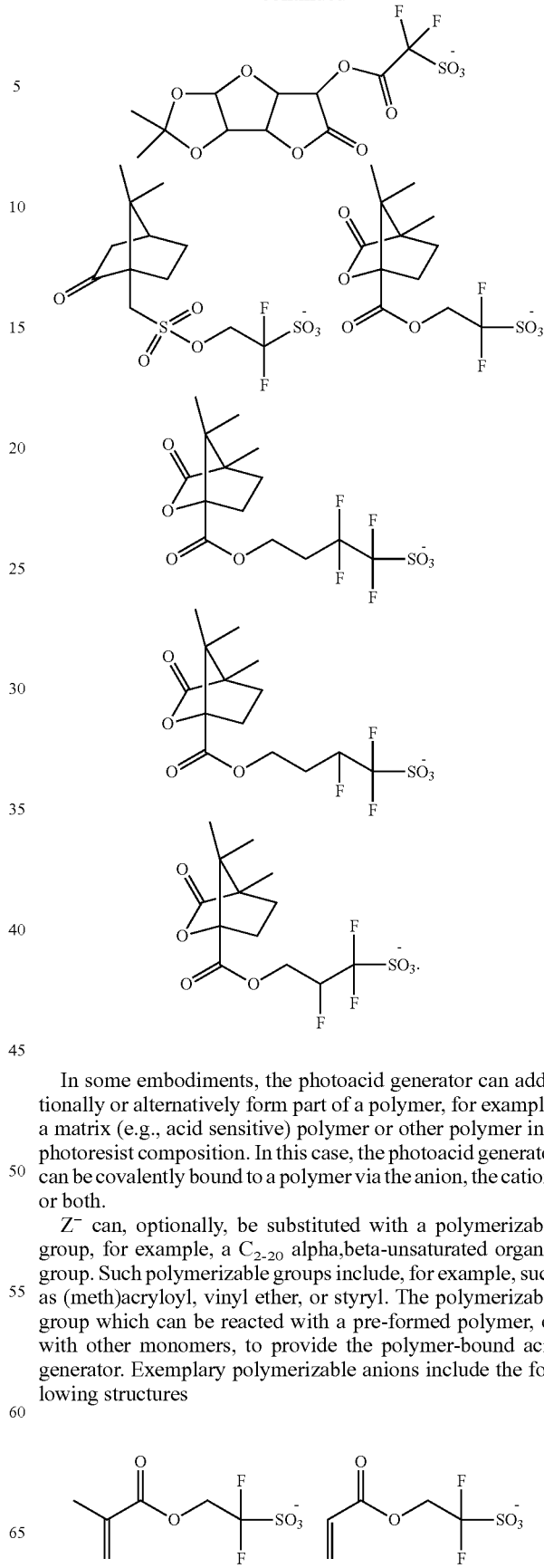

In some embodiments, the photoacid generator can additionally or alternatively form part of a polymer, for example, a matrix (e.g., acid sensitive) polymer or other polymer in a photoresist composition. In this case, the photoacid generator can be covalently bound to a polymer via the anion, the cation, or both.

$Z^-$ can, optionally, be substituted with a polymerizable group, for example, a $C_{2-20}$ alpha,beta-unsaturated organic group. Such polymerizable groups include, for example, such as (meth)acryloyl, vinyl ether, or styryl. The polymerizable group which can be reacted with a pre-formed polymer, or with other monomers, to provide the polymer-bound acid generator. Exemplary polymerizable anions include the following structures -continued

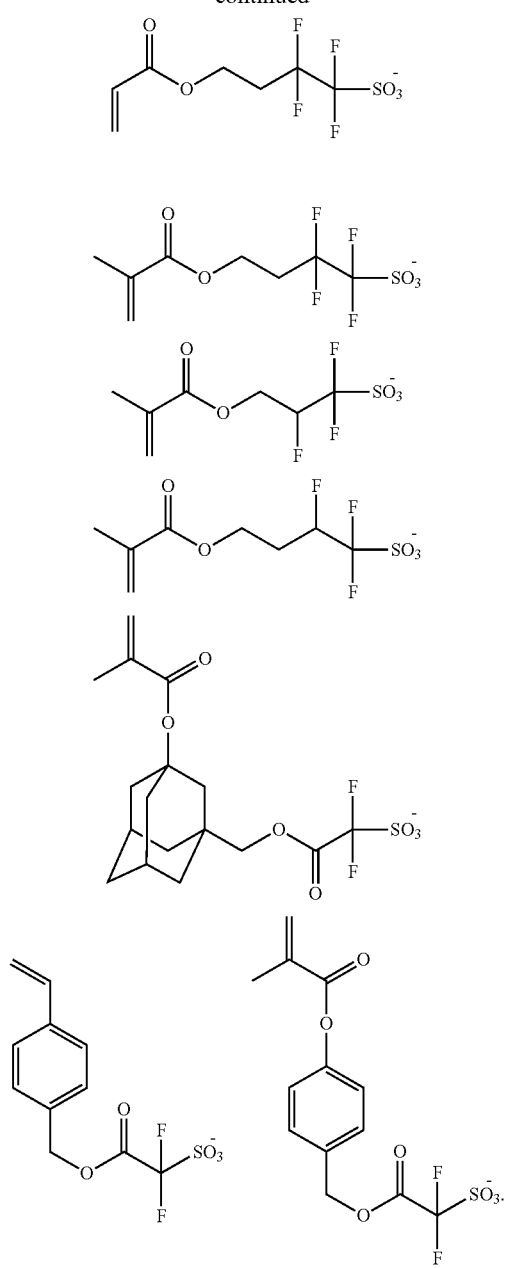

Exemplary polymerizable cations include the following structures

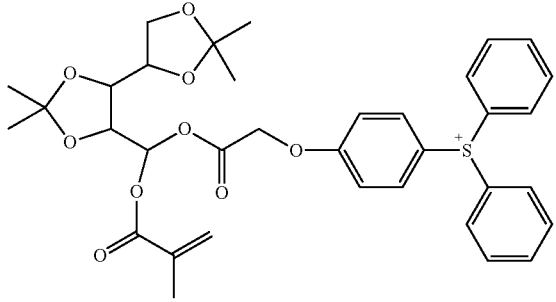

-continued

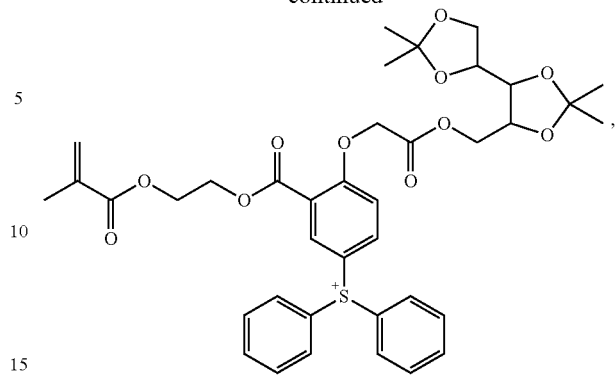

In terms of the photoacid generator structure of formula (1) above, the polymerizable group on the left structure is a substituent on $L^1$, and the polymerizable group on the right structure is a substituent on $L^4$.

The monomers used to form the photosensitive copolymer comprise an acid-sensitive monomer. Any sensitive (acid-deprotectable) monomer useful for forming a 193 nanometer photoresist polymer can be used. Acid-deprotectable monomers include tertiary alkyl (meth)acrylates such as, for example,

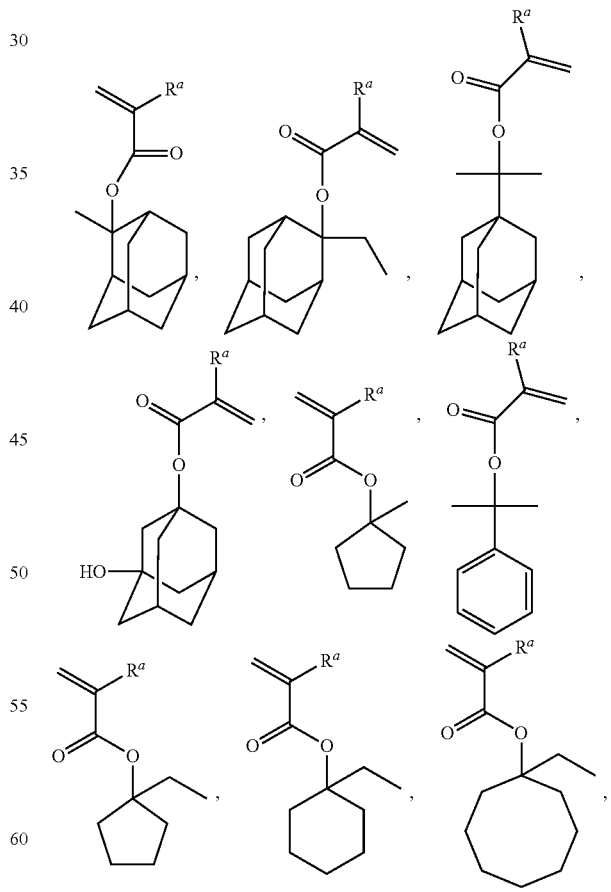

and combinations thereof, wherein $R^a$ is H, F, CN, $C_{1-10}$ alkyl, or $C_{1-10}$ fluoroalkyl. Additional types of acid-sensitive monomers include acetal- and ketal-substituted (meth)acrylate esters including, for example,

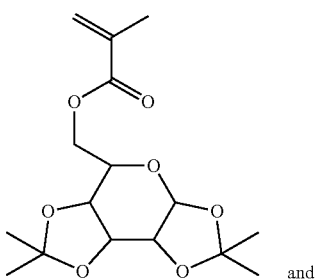

and

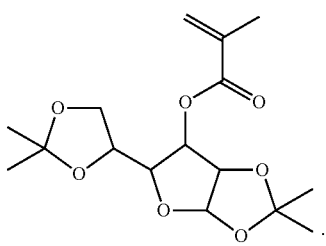

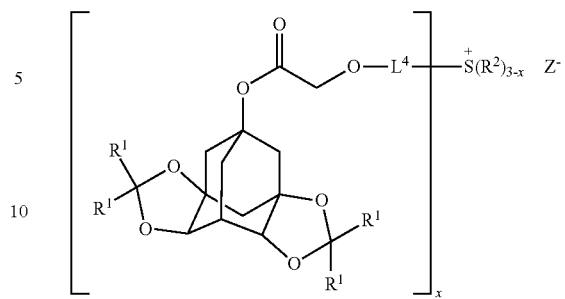

(2b)

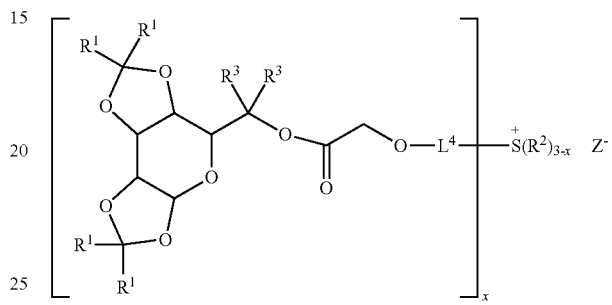

(2c)

Other monomers used to form the photosensitive copolymer can, optionally, further comprise base-soluble monomers, dissolution rate modifying monomers, etch-resistant monomers, photoacid acid generator monomers, and combinations thereof. These comonomers are described above and/or below in the context of the acid-sensitive polymer.

In a specific embodiment of the photoacid generator of formula (1), a is 1 at each occurrence; b is 1; c and d are as defined for formula (1); e is 1; x is 1; $L^1$ and $L^3$ are each independently a single bond, or an unsubstituted or substituted $C_{1-20}$ aliphatic group; wherein $L^1$ and $L^3$ are optionally directly covalently linked; $L^2$ is as defined for formula (1); $L^4$ is independently at each occurrence an unsubstituted or substituted $C_{6-20}$ arylene; $R^1$ is independently at each occurrence hydrogen, an unsubstituted $C_{1-12}$ linear or branched alkyl, an unsubstituted $C_{3-12}$ cycloalkyl, or an unsubstituted or substituted $C_{6-12}$ aryl; $R^2$ is independently at each occurrence an unsubstituted or substituted $C_{6-40}$ aryl; wherein when x is 1, the two groups $R^2$ are optionally directly covalently linked to each other; X is —O—C(O)—CH$_2$—O—; and $Z^-$ is an organic sulfonate anion.

In other specific embodiments, the photoacid generator compound has one of formulae (2a), (2b), and (2c)

(2a)

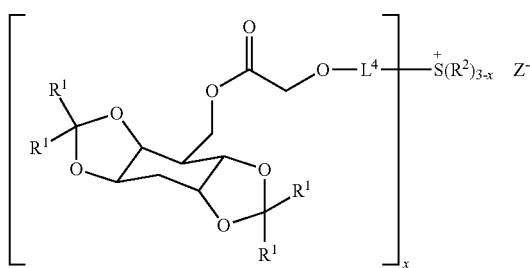

wherein $R^3$ is independently at each occurrence hydrogen, an unsubstituted or substituted $C_{1-30}$ linear or branched alkyl, an unsubstituted or substituted $C_{3-30}$ cycloalkyl, an unsubstituted or substituted $C_{6-30}$ aryl, or an unsubstituted or substituted $C_{3-30}$ heteroaryl; wherein each occurrence of $R^3$ is optionally covalently linked to the adjacent occurrence of $R^3$; and x, $L^4$, $R^1$, $R^2$, and $Z^-$ are defined as for formula (1).

In other specific embodiments, the photoacid generator compound has one of formulae (3a) and (3b)

(3a)

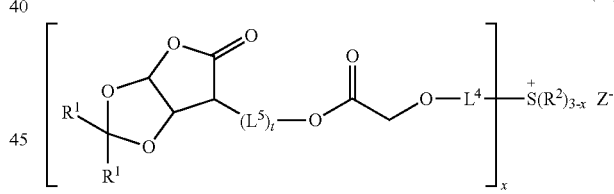

(3b)

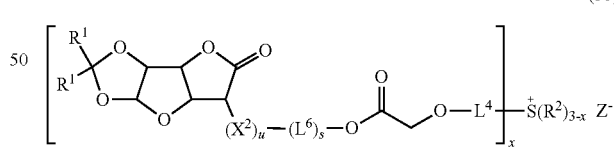

wherein s is independently at each occurrence 0 or 1; t is independently at each occurrence 0 or 1; u is independently at each occurrence 0 or 1; $L^5$ and $L^6$ are each independently at each occurrence an unsubstituted or substituted $C_{1-20}$ linear or branched alkylene, an unsubstituted or substituted $C_{3-20}$ cycloalkylene, or an unsubstituted or substituted $C_{6-20}$ arylene; $X^2$ is independently at each occurrence —O— or —N(R)—, wherein R is hydrogen or $C_{1-6}$ alkyl, and x, $L^4$, $R^1$, $R^2$, and $Z^-$ are as defined for formula (1).

In other specific embodiments, the photoacid generator compound has one of formulae (4a), (4b), (4c), (4d), (4e), and (4f)

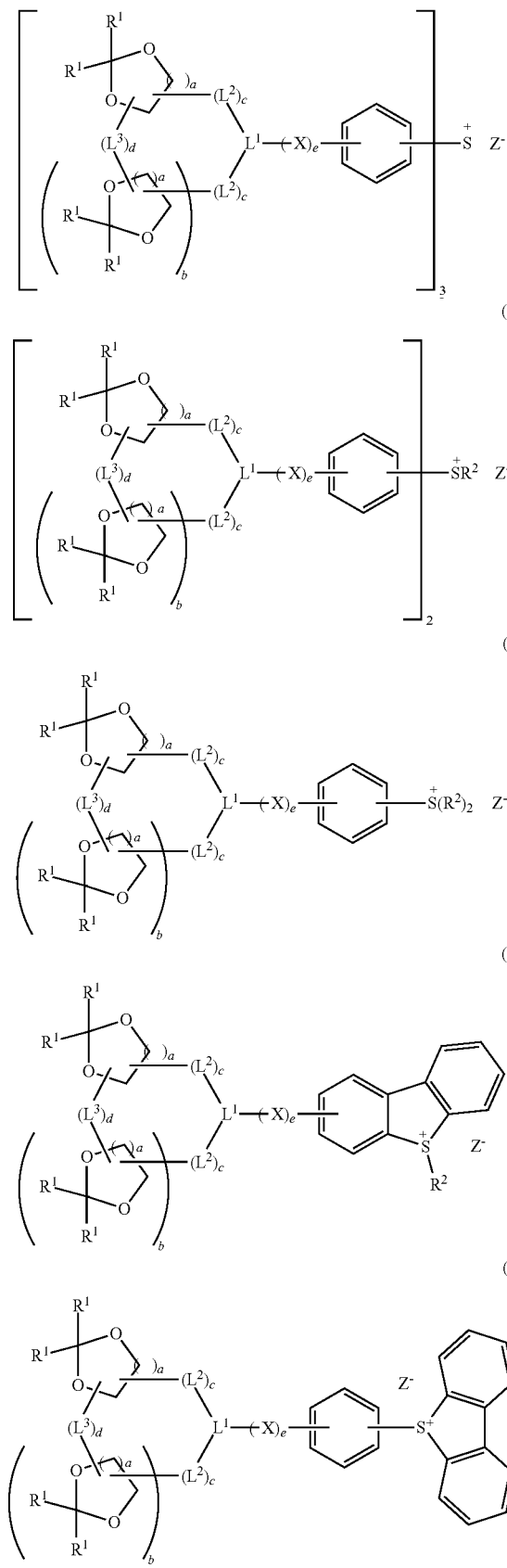
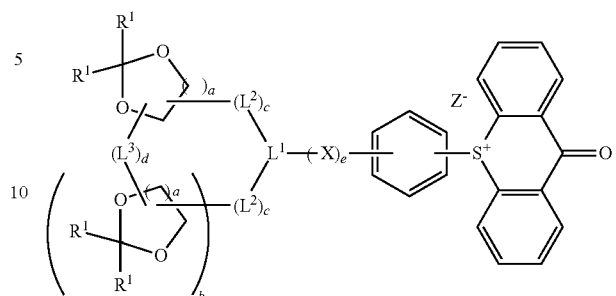

wherein a, b, c, d, e, $L^1$, $L^2$, $L^3$, $R^1$, $R^2$, X, and $Z^-$ are defined for formula (1).

In a very specific embodiment, the photoacid generator compound is selected from

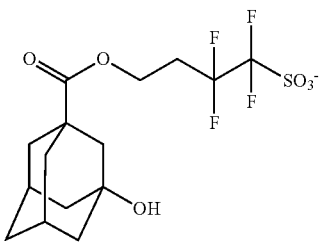

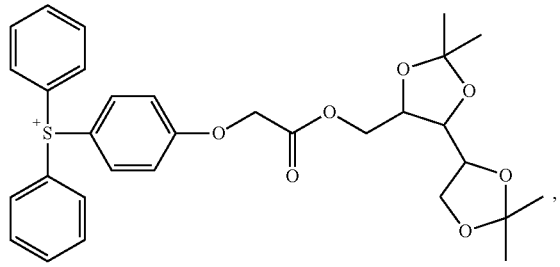

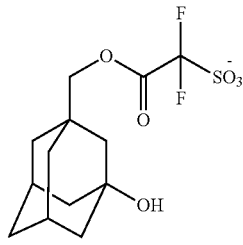

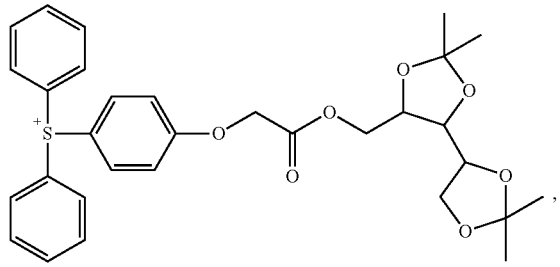

and combinations thereof

The photoacid generator compound is a useful component of photoresist compositions. Thus, one embodiment is a photoresist composition comprising: an acid-sensitive polymer, and the photoacid generator compound in any of its above-described variations. Acid-sensitive polymers useful for forming a photoresist in combination with the photoacid generator compound include the copolymerization products of monomers comprising acid-deprotectable monomers, base-soluble monomers, dissolution rate modifying monomers, and etch-resistant monomers. Any such monomers or combinations of monomers suitable for forming, for example, a 193 nanometer photoresist polymer can be used. In some embodiments, a combination of monomers is used, which include at least two different monomers selected from a (meth)acrylate monomer having an acid-deprotectable group (deprotection of which yields a base-soluble group), a (meth)acrylate monomer having a lactone functional group, and a (meth)acrylate monomer having a base-soluble group not identical to the acid-deprotectable base soluble group. The acid-sensitive polymer can include at least three different monomers, at least one of which is selected from each of the foregoing monomer types. Other monomers, such as a (meth)acrylate monomer for improving adhesion or etch-resistance, can also be included.

Any acid-deprotectable monomer useful for forming a 193 nanometer photoresist polymer can be used. These include the tertiary alkyl (meth)acrylates and acetal- and ketal-substituted (meth)acrylate esters described above in the context of the photosensitive copolymer.

Any lactone-containing monomer useful for forming a 193 nanometer photoresist polymer can be used. Exemplary such lactone-containing monomers include

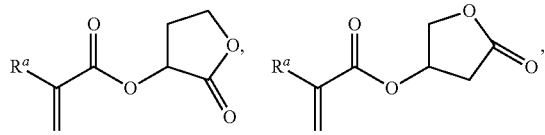

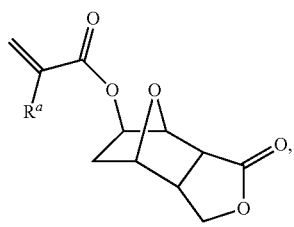

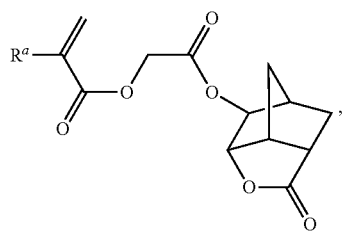

and combinations thereof, wherein $R^a$ is H, F, CN, $C_{1-10}$ alkyl, or $C_{1-10}$ fluoroalkyl.

Any base-soluble monomer useful for forming a 193 nanometer photoresist polymer can be used. Exemplary additional base-soluble (meth)acrylate monomers include

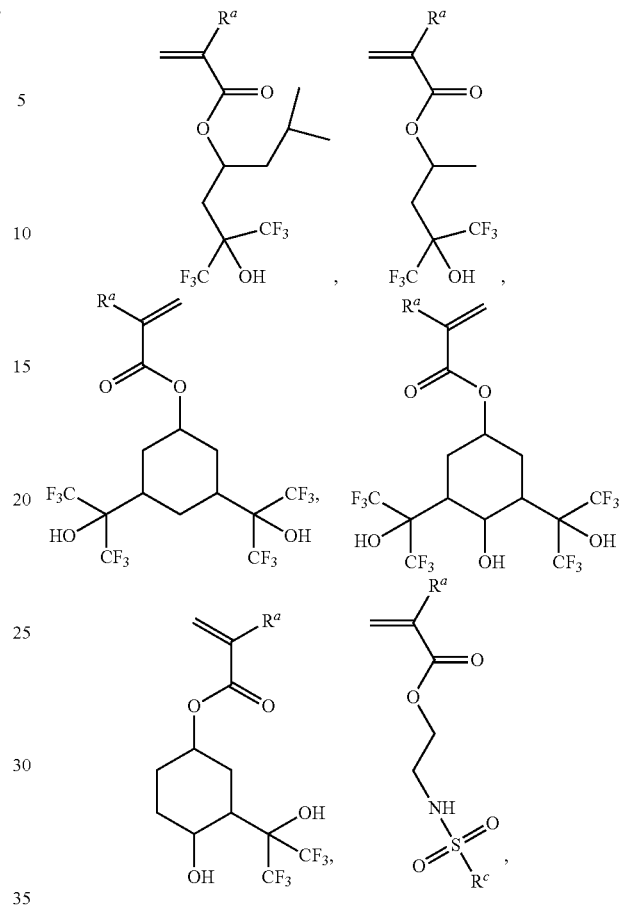

and combinations thereof, wherein $R^a$ is H, F, CN, $C_{1-10}$ alkyl, or $C_{1-10}$ fluoroalkyl, and $R^c$ is a $C_{1-4}$ perfluoroalkyl group.

The photoacid generator compound is combined with the acid-sensitive polymer, either in admixture or by copolymerization, to form a photoresist composition. The photoresist composition optionally further includes a second acid-sensitive polymer, a second photoacid generator compound, an amine or amide additive to adjust photospeed and/or acid diffusion, a solvent, a surfactant, or a combination thereof.

The second acid-sensitive polymer can be any polymer suitable for formulating photoresists for use with 193 nanometer or electron beam radiation. Such acid-sensitive polymers include an acid sensitive polymer comprising acid sensitive groups and lactone-containing groups, where the acid sensitive group deprotects a base-soluble group on exposure to acid.

The photoresist composition can include an amine or amide compound, referred to herein as a quencher. Quenchers can more broadly include, for example, those based on hydroxides, carboxylates, amines, imines, and amides. In some embodiments, the quencher comprises an amine, an amide, or a combination thereof. Specifically, such quenchers include $C_{1-30}$ organic amines, imines, or amides, or can be a $C_{1-30}$ quaternary ammonium salt of a strong base (e.g., a hydroxide or alkoxide) or a weak base (e.g., a carboxylate). Exemplary quenchers include amines such as Troger's base, a hindered amine such as diazabicycloundecene (DBU) or diazabicyclononene (DBN), N-protected amines such as N-t-butylcarbonyl-1,1-bis(hydroxymethyl)-2-hydroxyethylamine, or ionic quenchers including quaternary alkyl ammonium salts such as tetrabutylammonium hydroxide (TBAH) or tetrabutyl ammonium lactate.

The photoresist composition can include a photodecomposable quencher (PDQ), for example those based on photo-decomposable cations such triarylsulfoinum or bisaryliodonium. Examples for PDQs include triphenylsulfonium hydroxide, triphenylsulfonium camphorsulfonate or t-butylphenyldibenzothiophenium 1-adamantanecarboxylate.

Solvents generally suitable for dissolving, dispensing, and coating the components include anisole, alcohols including ethyl lactate, methyl 2-hydroxybutyrate (HBM), 1-methoxy-2-propanol (also referred to as propylene glycol methyl ether, PGME), and 1-ethoxy-2 propanol, esters including n-butyl acetate, 1-methoxy-2-propyl acetate (also referred to as propylene glycol methyl ether acetate, PGMEA), methoxyethyl propionate, ethoxyethyl propionate, and gamma-butyrolactone, ketones including cyclohexanone and 2-heptanone, and combinations thereof.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX™ PF-636, PF-6320, PF-656, and PF-6520 fluorosurfactants from Omnova.

The photoacid generator compound is present in the photoresist in an amount of 0.01 to 40 weight percent, specifically 0.1 to 20 weight percent, based on the total weight of solids in the photoresist composition. Where a polymer-bound photoacid generator is used, the polymer-bound photoacid generator as the corresponding monomer is present in the same amount. In some embodiments, photoresist composition comprises polymer-bound photoacid generator and a photoacid generator additive. The polymer content can be present in an amount of 50 to 99 weight percent, specifically 55 to 95 weight percent, more specifically 60 to 90 weight percent, and still more specifically 65 to 90 based on the total weight of solids in the photoresist composition. It will be understood that "polymer" used in this context of a component in a photoresist can mean only the acid-sensitive polymer described herein, or a combination of the acid-sensitive polymer with another polymer useful in a photoresist. A surfactant can be included in an amount of 0.01 to 5 weight percent, specifically 0.1 to 4 weight percent, and still more specifically 0.2 to 3 weight percent, based on the total weight of solids in the photoresist composition. Other additives such as embedded barrier layer (EBL) materials for immersion lithography applications can be included in amounts of less than or equal to 30 weight percent, specifically less than or equal to 20 weight percent, or more specifically less than or equal to 10 weight percent, based on the total weight of solids. The total solids content of the photoresist composition can be 0.5 to 50 weight percent, specifically 1 to 45 weight percent, more specifically 2 to 40 weight percent, and still more specifically 5 to 35 weight percent, based on the total weight of solids and solvent. It will be understood that the "solids" includes copolymer, photoacid generator, quencher, surfactant, and any optional additives, exclusive of solvent.

The photoresist disclosed herein can be used to form a film comprising the photoresist, where the film on the substrate constitutes a coated substrate. Such a coated substrate includes: (a) a substrate having one or more layers to be patterned on a surface thereof; and (b) a layer of the photoresist composition over the one or more layers to be patterned. Preferably, patterning is carried out using ultraviolet radiation at wavelength of less than 248 nm, and in particular, at 193 nm. The patternable film thus comprises the photoacid generator compound. A method of forming an electronic device includes: (a) applying a layer of the photoresist composition on a substrate; (b) pattern-wise exposing the photoresist composition layer to activating radiation; and (c) developing the exposed photoresist composition layer to provide a resist relief image. In some embodiments, the radiation is extreme ultraviolet (EUV) or electron beam (e-beam) radiation.

Developing the pattern can be accomplished by either positive tone development (PTD) in which the pattern-wise exposed region is removed by the action of an aqueous base developer such as aqueous tetramethylammonium hydroxide (TMAH). An exemplary positive tone developer is 0.26 Normal aqueous TMAH. Alternatively, the same pattern-wise exposure can be developed using an organic solvent developer to provide a negative tone development (NTD) in which the unexposed region of a pattern is removed by the action of a negative tone developer. Useful solvents for negative tone development include those also useful for dissolving, dispensing, and coating. Exemplary negative tone developer solvents include propylene glycol methyl ether acetate (PGMEA), methyl 2-hydroxyisobutyrate (HBM), methoxyethyl propionate, ethoxyethyl propionate, and gamma-butyrolactone, cyclohexanone, 2-heptanone, and combinations thereof. A method of making a pattern thus includes pattern-wise exposing a photoresist composition layer with actinic radiation, and developing the pattern by treatment with an aqueous alkaline developer to form a positive tone relief image, or with an organic solvent developer to form a negative tone relief image.

Substrates can be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. The surfaces of substrates herein can include critical dimension layers to be patterned including, for example, one or more gate-level layers or other critical dimension layer on the substrates for semiconductor manufacture. The substrates can be formed as circular wafers having dimensions such as, for example, 200 millimeters, 300 millimeters, or larger in diameter, or other dimensions useful for wafer fabrication.

The invention is further illustrated by the following working examples.

SYNTHESIS OF PAG-A1

The synthesis of PAG-A1 is summarized in FIG. 1, where "TEA" is triethylamine, "DCM" is dichloromethane, "rt" is room temperature (i.e., about 23° C.), "16 h" is 16 hours, "$K_2CO_3$" is potassium carbonate, "$CH_3CN$" is acetonitrile, and "50C" is 50° C.

(2,2,2',2'-tetramethyl-4,4'-bis(1,3-dioxolan)-5-yl)methyl 2-chloroacetate (1): To a mixture of (2,2,2',2'-tetramethyl-4,4'-bis(1,3-dioxolan)-5-yl)methanol (80 grams, 0.34 mole) and triethylamine (70 grams, 0.69 mole) in dichloromethane (400 milliliters) at 0° C. was added chloroacetyl chloride (39 grams, 0.34 mole) drop-wise over 1-3 hours with the temperature controlled below 10° C. After complete addition, the mixture was stirred at room temperature for 24 hours. The reaction mixture was filtered and the organic solution was washed with water twice. The organic solution was passed through a silica plug initially using dichloromethane as eluting solvent followed by ethyl acetate. Solvent was evaporated from the resulting organic solution to give pure product (1) as a pale brown viscous oil in 70% yield (70 grams). $^1$H NMR (CDCl$_3$, 300 MHz): δ 1.40 (s, 3H), 1.46 (s, 9H), 3.88 (m, 2H), 4.09 (m, 1H), 4.15 (s, 2H), 4.20 (m, 3H), 4.40 (m, 1H).

4-(2-oxo-2-(2,2,2',2'-tetramethyl-4,4'-bis(1,3-dioxolan)-5-yl-methoxyethoxy)phenyl)diphenylsulfonium iodide (3): 4-Hydroxyphenyl)diphenylsulfonium iodide (2, 9.66 grams, 0.027 mole) was dissolved in anhydrous acetonitrile. After complete dissolution, potassium carbonate (18.6 grams, 0.135 mole) was added followed by addition of (2,2,2',2'-tetramethyl-4,4'-bis(1,3-dioxolan)-5-yl)methyl 2-chloroacetate) (1, 10.00 grams, 0.032 mole). The reaction mixture was refluxed overnight. The reaction mixture was cooled to room temperature and filtered. Solvent was evaporated from the filtrate on a rotary evaporator, and the residual oily material was dissolved in dichloromethane (200 milliliters), washed with H$_2$O (100 milliliters), dried on MgSO$_4$, and the solvent removed under reduced pressure to give a clear oil. The oil was redissolved in a minimal amount of methylene chloride and precipitated in a large excess of methyl tert-butyl ether (MTBE) to give a white solid which was filtered and dried under vacuum to give 17.6 grams (96% yield) of oily product (3). $^1$H NMR (CDCl$_3$, 300 MHz): δ 1.37 (s, 3H), 1.42 (bs, 9H), 3.9 (m, 2H), 4.09 (t, 1H), 4.23 (m, 3H), 4.45 (m, 1H), 4.82 (s, 2H), 7.23 (d, 2H), 7.73 (m, 10H), 7.92 (d, 2H).

4-(2-oxo-2-(2,2,2',2'-tetramethyl-4,4'-bis(1,3-dioxolan)-5-yl-methoxyethoxy)phenyl)diphenylsulfonium 1-adamantyl-3,3,4,4-tetrafluorobutane sulfonate (abbreviated IPXPDPS ADOH TFBS (PAG-A1)): 4-(2-oxo-2-(2,2,2',2'-tetramethyl-4,4'-bis(1,3-dioxolan)-5-yl)methoxyethoxy) phenyl)diphenylsulfonium iodide (IPXPDPSI) (3, 12.12 grams, 17.86 millimoles) and sodium 1-adamantyl-3,3,4,4-tetrafluorobutane sulfonate (4) (8.0 grams, 18.76 millimoles) were dissolved in 150 milliliters dichloromethane and 150 milliliters deionized water and stirred at room temperature for 16 hours. The reaction was stopped and the organic layer was separated and washed five times with 150 milliliter volumes of deionized water. The organic solvent was removed under reduced pressure to produce the crude product as an oil. The oil was dissolved in dichloromethane (100 milliliters) and poured slowly into 1 liter methyl tert-butyl ether (MTBE). The white solids were collected and dried under vacuum to yield 13 grams (76% yield) of IPXPDPS ADOH TFBS (PAG-A1). $^1$H NMR (CDCl$_3$, 300 MHz): δ 1.35 (s, 3H), 1.41 (bs, 9H), 1.5-1.8 (m, 12H), 2.21 (s, 1H), 2.7 (m, 2H), 3.9 (m, 2H), 4.07 (t, 1H), 4.22 (m, 3H), 4.31 (t, 2H), 4.43 (m, 1H), 4.81 (s, 2H), 7.23 (d, 2H), 7.67 (m, 10H), 7.73 (d, 2H). $^{19}$F NMR: δ −118.46, −112.48.

SYNTHESIS OF PAG-A2

Figure 2:
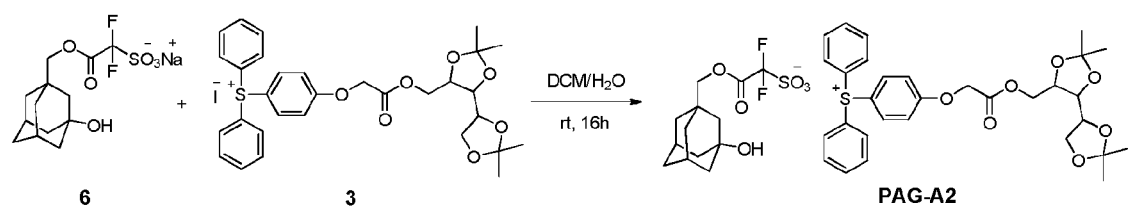
FIG. 2 is a synthetic scheme illustrating the synthesis of the photoacid generator PAG-A2.

The synthesis of PAG-A2 is summarized in FIG. 2.

4-(2-oxo-2-(2,2,2',2'-tetramethyl-4,4'-bis(1,3-dioxolan)-5-yl-methoxyethoxy)phenyl)diphenylsulfonium 1,1-difluoro-2-(3-hydroxyadamantan-1-yl-methoxy)-2-oxoethane-sulfonate (abbreviated IPXPDPS ADOH-CDFMS (PAG-A2)): 4-(2-oxo-2-(2,2,2',2'-tetramethyl-4,4'-bis(1,3-dioxolan)-5-yl-methoxyethoxy)phenyl)diphenylsulfonium iodide (IPXPDPSI) (3, 10 grams, 14.73 millimoles) and sodium 1,1-difluoro-2-((-3-hydroxyadamantan-1-yl)methoxy)-2-oxoethanesulfonate (8, 5.62 grams, 15.49 millimoles) were dissolved in 150 milliliters dichloromethane and 150 milliliters deionized water and stirred at room temperature for 16 hours under nitrogen. The reaction was stopped and the organic layer was separated and washed five times with 150 milliliter volumes of deionized water. The organic solvent was removed under reduced pressure to produce an oil. The oil was dissolved in dichloromethane (100 milliliters) and poured slowly into 1 liter methyl tert-butyl ether (MTBE). The white suspension was stirred 1 hour and allowed to stand for 30 minutes, after which the white solids were collected and dried under vacuum to yield 11 grams (83.7% yield) of IPXPDPS ADOH CDFMS (PAG-A2). $^1$H NMR (CDCl$_3$, 300 MHz): δ 1.35 (s, 3H), 1.41 (bs, 9H), 1.46-1.6 (m, 12H), 2.16 (s, 1H), 3.89 (m, 4H), 4.08 (t, 1H), 4.22 (m, 3H), 4.43 (m, 1H), 4.81 (s, 2H), 7.23 (d, 2H), 7.69 (m, 10H), 7.77 (d, 2H). $^{19}$F NMR: δ −109.75.

Solubility Evaluation

The photoacid generators were evaluated for solubility in a selection of organic solvents. Solubility of each of the compounds PAG-2, PAG-A1, PAG-A2 were obtained for attempts to completely dissolve the PAG at 2 weight percent at room temperature in different organic solvents and solvent blends. The results for the solubility tests (i.e., where the PAG is observed to be completely soluble in the solvent, or is only partially soluble or insoluble based on the presence of insoluble material) are shown in Table 1, where "O" indicates solubility at 2 weight percent, and "X" indicates partial solubility or insolubility at 2 weight percent.

TABLE 1

| Solvent | PAG-2 | PAG-A1 | PAG-A2 |
| --- | --- | --- | --- |
| PGMEA | X | O | O |
| 2-Heptanone | X | O | O |
| 2-Hepanone/n-Butyl Propionate (1:1 w/w) | X | O | O |
| n-Butyl Acetate | X | O | O |

The solubility results in Table 1 indicate that the photoacid generators comprising ketal groups (PAG-A1 and PAG-A2) are soluble in solvents at concentrations useful for formulating photoresist compositions and in the negative tone developer solvent n-butyl acetate. The inclusion of ketal group on the cationic portion of the PAG thus increases solubility of the PAG cation/anion pair in organic solvents having a range of polarities.

Lithographic Evaluation Using Positive Tone Development

The photoacid generators were evaluated lithographically according to the following procedure. Photoresists were formulated using the components and proportions shown in Table 3. The photoresist polymer A2 was used in all examples. Polymer A2 is a pentapolymer incorporating monomers M1, M2, M3, M4 and M5, having the following structures

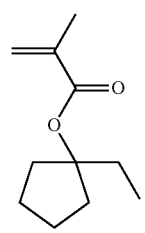

M1

M2
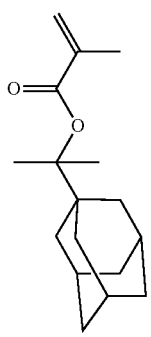

M3
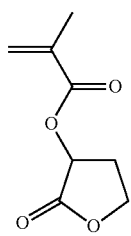

M4
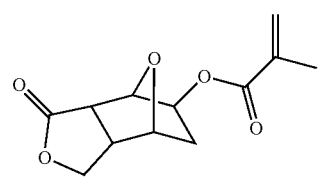

M5
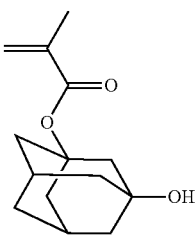

where the mole percentage of M1/M2/M3/M4/M5 is 20/20/30/20/10 for a total of 100 mole percent of monomers. The weight average molecular weight of the polymer A2 was 8,000 grams/mole. Note that in Table 3, the amounts of PAG, base (t-butyloxycarbonyl-4-hydroxypyridine, TBOC-4HP), and surface leveling agent (SLA; surfactant) PF 656, available from Omnova, are in weight percent based on 100% solids content, with the balance of the solids being the polymer. The solvents used in these formulations are propylene glycol methyl ether acetate (PGMEA; S1) and methyl 2-hydroxybutyrate (HBM; S2). The final percent solids in both examples were 4 weight percent. The weight ratio of solvents S1:S2 in the final formulation was 1:1. Structures of the comparative PAGs are shown in Table 2.

TABLE 2

| PAG | PAG Chemical Name | PAG Structure |
|---|---|---|
| Comparative PAG 1 | Triphenyl-sulfonium perfluoro-butane-sulfonate | |
| Comparative PAG 2 | Triphenyl-sulfonium 1,1-difluoro-2-((-3-hydroxy-adamantan-1-yl)methoxy)-2-oxoethane-sulfonate | |

Photoresist formulation compositions for Comparative Example and Examples 1 and 2 are shown in Table 3.

TABLE 3

| Sample | PAG | PAG (wt %) | Base (wt %) | SLA (wt %) |
|---|---|---|---|---|
| Comparative Example 1 | Comparative PAG 1 | 9.59 | 1.03 | 0.1 |
| Comparative Example 2 | Comparative PAG 2 | 10.27 | 1.03 | 0.1 |
| Example 1 | PAG-A1 | 16.28 | 1.03 | 0.1 |
| Example 2 | PAG-A2 | 15.19 | 1.03 | 0.1 |

The above photoresists were lithographically processed as follows. The photoresist was spin coated onto a 200 millimeter silicon wafer having 84 nanometers of an organic antireflective coating (AR™77, Dow Electronic Materials) and baked at 110° C. for 60 seconds, to form a resist film 100 nanometers in thickness. The photoresist was exposed with an ArF excimer laser (193 nanometers) through a mask pattern targeting a line and space pattern (L/S pattern) having a line width of 90 nanometers and a pitch of 180 nanometers, using an ArF exposure apparatus ASML-1100 (manufactured by ASML), numerical aperture (NA)=0.75 under annular illumination with outer/inner sigma of 0.89/0.64 with focus offset/step 0.10/0.05. The wafers were post exposure baked (PEB) at 100° C. for 60 seconds followed by developing with 0.26 N aqueous tetramethylammonium hydroxide (TMAH) developer and subsequent water wash.

Mask Error Factor (MEF) and Exposure Latitude (EL) were determined by processing the image captured by top-down scanning electron microscopy (SEM) using a Hitachi 9380 CD-SEM, operating at an accelerating voltage of 800 volts (V), probe current of 8.0 picoamperes (pA), using 200,000× magnification. In Table 4, "$E_0$" is the dose to clear and is expressed in millijoules/centimeter$^2$; "$E_s$", or sizing energy, is the exposure required to produce the proper dimension of the resist feature and is expressed in millijoules/centimeter$^2$; "CD", or critical dimension, is the minimum feature size and is expressed in nanometers; "EL", or exposure latitude, is the difference in exposure energy to print +/−10% of the target diameter normalized by the sizing energy and is expressed in percent; "MEF", or mask error factor, is the ratio of CD change on the resolved resist pattern to the relative dimension change on the mask pattern, and is unitless; "LWR", or line width roughness, is the, calculated as 3 σ (three standard deviations) from the feature edge (as viewed top down) from a smooth ideal shape at the stated critical dimension (CD) and at best focus and at the stated sizing energy ($E_s$), and is expressed in nanometers (nm).

The results from the lithographic evaluation of the above photoresist formulations are reported in Table 4. The data in Table 4 show that, relative to Comparative Example 1 using Comparative PAG 1, Examples 1 and 2 using PAG-A1 and PAG-A2, respectively, exhibit improved exposure latitude (EL) and mask error factor (MEF). Although Comparative Example 2 with Comparative PAG 2 exhibits superior exposure latitude and mask error factor relative to Examples 1 and 2, as demonstrated below a photoresist with Comparative PAG 2 exhibits inferior Critical Dimension Uniformity in a Negative Tone Development process.

TABLE 4

| PAG | C. Ex. 1<br>C. PAG 1 | C. Ex. 2<br>C. PAG 2 | Ex. 1<br>PAG-A1 | Ex. 2<br>PAG-A2 |
|---|---|---|---|---|
| $E_0$ (mJ/cm$^2$) | 5.6 | 9.6 | 10.0 | 17.4 |
| $E_s$ (mJ/cm$^2$) | 24.6 | 45.9 | 48.0 | 67.0 |
| CD (nm) | 91.62 | 91.49 | 91.27 | 91.41 |
| EL (%) | 6.99 | 9.47 | 8.64 | 8.10 |
| MEF | 4.04 | 3.45 | 3.67 | 3.53 |
| LWR (nm) | 12.0 | 12.4 | 12.8 | 13.2 |

Lithographic Evaluation Using Negative Tone Development

The photoacid generators were evaluated lithographically using negative tone development according to the following procedure. Photoresists were formulated using the components and proportions shown in Table 5. The photoresist polymer A3 was used in all examples. Polymer A3 has the composition shown below.

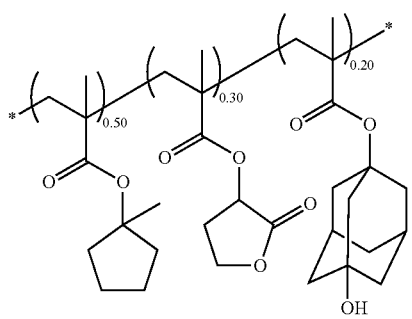

The embedded barrier layer (EBL) was poly(n-butyl methacrylate)/poly(isobutyl methacrylate) in a 25:75 weight ratio in iso-butyl butyrate. The base component was N,N-diethanoldodecanamine (DDEA). Note that in Table 5, the photoacid generator, base, and EBL amounts are in weight percent based on 100% solids content. The solvents used in these formulations are propylene glycol methyl ether acetate (S1) and methyl 2-hydroxybutyrate (S2). The final percent solids in both examples was 4 weight percent. The weight ratio of solvents S1:S2 in the final formulation was 1:1.

TABLE 5

| Photoresist | Polymer A3 (%) | Compar. PAG 2 (%) | PAG-A2 (%) | Base (%) | EBL (%) |
|---|---|---|---|---|---|
| C. Ex. 3 | 86.204 | 11.046 | 0 | 0.75 | 2.0 |
| Ex. 3 | 80.920 | 0 | 16.330 | 0.75 | 2.0 |

Immersion lithography was carried out on 300 millimeter silicon wafers using an ASML Twinscan XT:1900i scanner. Silicon wafers were spin-coated with AR™40A antireflectant (Rohm and Haas Electronic Materials) and baked for 60 seconds at 215° C. to yield a first Bottom Anti-Reflective Coating (BARC) film with a thickness of 840 Angstroms. A second BARC layer was next coated over the first BARC using AR™124 antireflectant (Rohm and Haas Electronic Materials), and was baked at 205° C. for 60 seconds to generate a 200 Angstrom top BARC layer. The photoresist was then coated on the dual BARC-coated wafers and soft-baked at 90° C. for 60 seconds to provide a resist layer with a thickness of 900 Angstroms. The photoresist-coated wafers were exposed with an immersion ArF exposure apparatus (ASML Twinscan XT:1900i) through a 6% attenuated phase-shifting mask under single exposure condition. The exposed wafers were post-exposure baked at 100° C. for 60 seconds and then developed using n-butyl acetate developer for 25 seconds on a TEL CLEAN TRACK LITHIUS i+ coater/developer to give negative tone patterns. $E_s$ is the optimum energy used to print 60/90 nm contact holes. Lithographic results for are collected in Table 6. As can be seen the two examples have the same exposure latitude values and Example 3 has a clear Critical Dimension Uniformity (CDU) improvement compared to Comparative Example 3. This indicates that use of the photoacid generators of the present of the present invention in negative tone development provides improved circularity of printed contact holes.

TABLE 6

| PAG | C. Ex. 3<br>C. PAG 2 | Ex. 3<br>PAG-A2 |
|---|---|---|
| $E_s$ (mJ/cm$^2$) | 29.6 | 40.1 |
| EL (%) | 9.9 | 9.9 |
| CDU (nm) | 7.12 | 6.42 |

The invention claimed is:

1. A photoacid generator compound having formula (1)

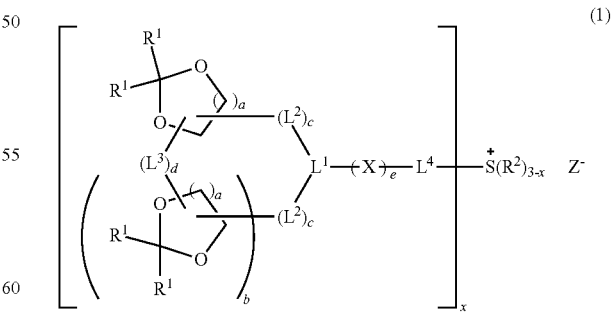

wherein
a is independently at each occurrence 0, 1, 2, 3, 4, 5, 6, 7, 8, 9, 10, 11, or 12;
b is independently at each occurrence 1, 2, 3, 4, or 5;
c is independently at each occurrence 0 or 1;

d is 0 or 1;
e is 1;
x is 1, 2, or 3;
L$^1$ and L$^3$ are each independently at each occurrence a single bond, an unsubstituted or substituted C$_{1-20}$ aliphatic group, an unsubstituted or substituted C$_{6-20}$ aromatic group, or an unsubstituted or substituted C$_{3-20}$ heteroaromatic group; wherein L$^1$ and L$^3$ are optionally directly covalently linked; and wherein one or more of L$^1$ and L$^3$ are optionally substituted with a polymerizable group;
L$^2$ is independently at each occurrence a single bond, a carbonyl group, an ester group, an amide group, an ether oxygen, or a C$_{1-20}$ aliphatic group optionally substituted with an ether oxygen, a carbonyl group, an ester group, an ether oxygen, or a combination thereof; wherein two occurrences of L$^2$ are optionally directly covalently linked; and wherein one or more occurrences of L$^2$ are optionally substituted with a polymerizable group;
L$^4$ is independently at each occurrence an unsubstituted or substituted C$_{6-20}$ arylene, an unsubstituted or substituted C$_{3-20}$ heteroarylene, an unsubstituted or substituted C$_{1-20}$ linear or branched alkylene, or an unsubstituted or substituted C$_{3-20}$ cycloalkylene; wherein L$^4$ is optionally covalently linked to an occurrence of R$^2$; and wherein one or more occurrences of L$^4$ are optionally substituted with a polymerizable group;
R$^1$ is independently at each occurrence hydrogen, an unsubstituted or substituted C$_{1-30}$ linear or branched alkyl, an unsubstituted or substituted C$_{3-30}$ cycloalkyl, an unsubstituted or substituted C$_{6-30}$ aryl, or an unsubstituted or substituted C$_{3-30}$ heteroaryl; wherein each occurrence of R$^1$ is optionally covalently linked to an adjacent occurrence of R$^1$; and wherein one or more occurrences of R$^1$ are optionally substituted with a polymerizable group;
R$^2$ is independently at each occurrence an unsubstituted or substituted C$_{6-40}$ aryl, an unsubstituted or substituted C$_{3-40}$ heteroaryl, an unsubstituted or substituted C$_{1-40}$ alkyl, or an unsubstituted or substituted C$_{3-40}$ cycloalkyl; wherein when x is 1, two groups R$^2$ are optionally directly covalently linked to each other; and wherein one or more occurrences of R$^2$ are optionally substituted with a polymerizable group;
X is independently at each occurrence an —O—, —S—, or an ether-, carbonyl-, ester-, carbonate-, amine-, amide-, urea-, sulfate-, sulfonate-, or sulfonamide-containing group, or combination thereof; wherein one or more occurrences of X are optionally substituted with a polymerizable group; and
Z$^-$ is an organic anion; wherein Z$^-$ is optionally substituted with a polymerizable group.
2. The photoacid generator compound of claim 1, wherein
a is 1 at each occurrence;
b is 1;
c and d are as defined in claim 1;
e is 1;
x is 1;
L$^1$ and L$^3$ are each independently at each occurrence a single bond, or an unsubstituted or substituted C$_{1-20}$ aliphatic group; wherein L$^1$ and L$^3$ are optionally directly covalently linked;
L$^2$ is as defined in claim 1;
L$^4$ is at each occurrence an unsubstituted or substituted C$_{6-20}$ arylene;

R$^1$ is independently at each occurrence hydrogen, an unsubstituted C$_{1-12}$ linear or branched alkyl, an unsubstituted C$_{3-12}$ cycloalkyl, or an unsubstituted or substituted C$_{6-12}$ aryl;
R$^2$ is independently at each occurrence an unsubstituted or substituted C$_{6-40}$ aryl; wherein when x is 1, the two groups R$^2$ are optionally directly covalently linked to each other;
X is —O—C(O)—CH$_2$—O— at each occurrence; and
Z$^-$ is an organic sulfonate anion.
3. The photoacid generator compound of claim 1, having one of formulae (2a), (2b), and (2c)

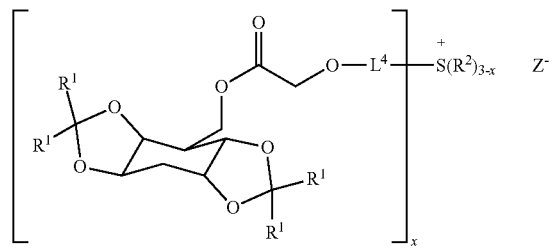

(2a)

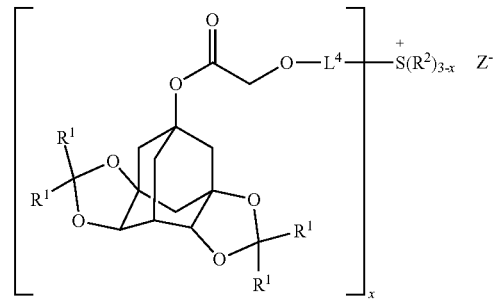

(2b)

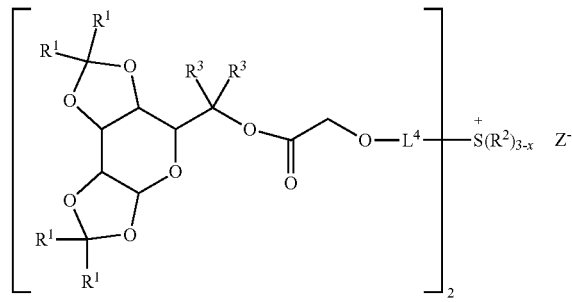

(2c)

wherein
R$^3$ is independently at each occurrence hydrogen, an unsubstituted or substituted C$_{1-30}$ linear or branched alkyl, an unsubstituted or substituted C$_{3-30}$ cycloalkyl, an unsubstituted or substituted C$_{6-30}$ aryl, or an unsubstituted or substituted C$_{3-30}$ heteroaryl; wherein each occurrence of R$^3$ is optionally covalently linked to an adjacent occurrence of R$^3$; and
x, L$^4$, R$^1$, R$^2$, and Z$^-$ are defined as in claim 1.

4. The photoacid generator compound of claim 1, having one of formulae (4a), (4b), (4c), (4d), (4e), and (4f),
(4a)
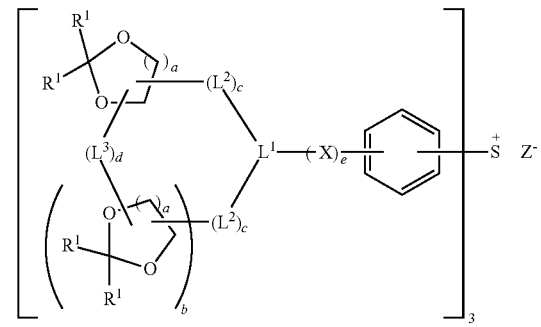
(4b)
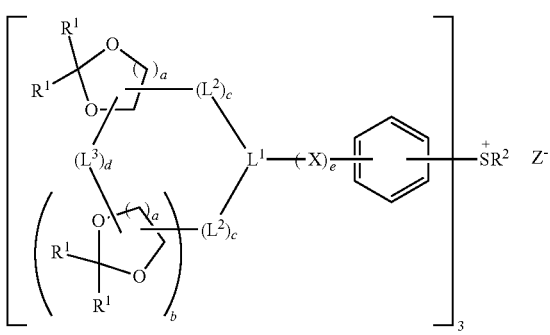
(4c)
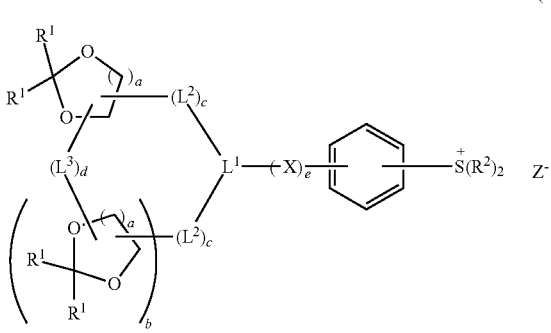
(4d)
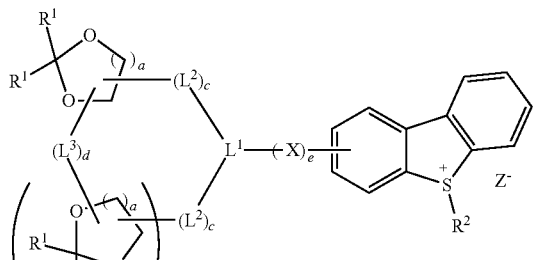
(4e)
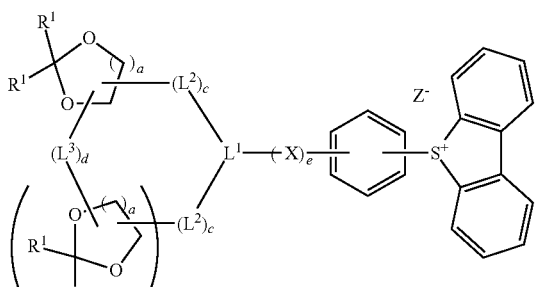
(4f)
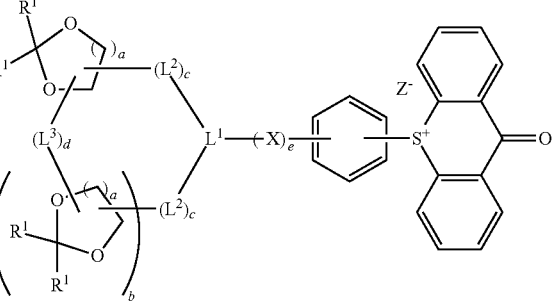
wherein a, b, c, d, e, $L^1$, $L^2$, $L^3$, $R^1$, $R^2$, X, and $Z^-$ are defined as in claim 1.
5. The photoacid generator compound of claim 1, selected from
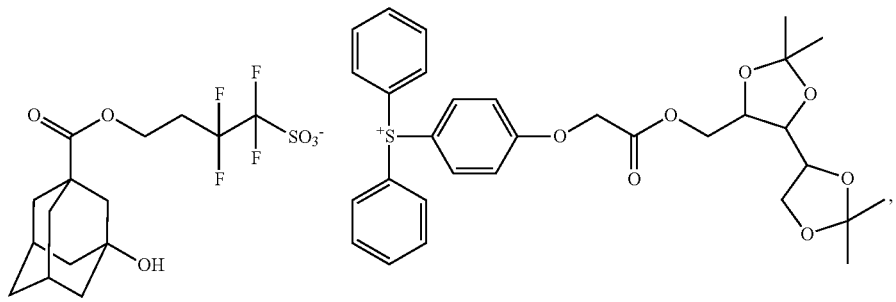

-continued

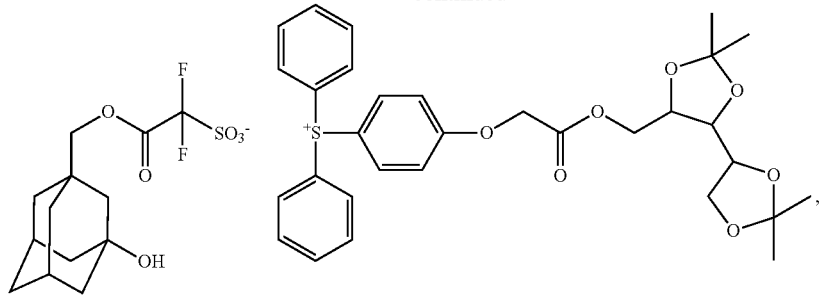

and combinations thereof.

6. A photoresist composition comprising an acid-sensitive polymer and the photoacid generator compound of claim 1.

7. A method of forming an electronic device, comprising:
(a) applying a layer of a photoresist composition of claim 6 on a substrate;
(b) pattern-wise exposing the photoresist composition layer to activating radiation; and
(c) developing the exposed photoresist composition layer to provide a resist relief image.

8. The photoresist composition of claim 6, wherein
a is 1 at each occurrence;
b is 1;
c and d are as defined in claim 1;
e is 1;
x is 1;
$L^1$ and $L^3$ are each independently at each occurrence a single bond, or an unsubstituted or substituted $C_{1-20}$ aliphatic group; wherein $L^1$ and $L^3$ are optionally directly covalently linked;
$L^2$ is as defined in claim 1;
$L^4$ is at each occurrence an unsubstituted or substituted $C_{6-20}$ arylene;
$R^1$ is independently at each occurrence hydrogen, an unsubstituted $C_{1-12}$ linear or branched alkyl, an unsubstituted $C_{3-12}$ cycloalkyl, or an unsubstituted or substituted $C_{6-12}$ aryl;
$R^2$ is independently at each occurrence an unsubstituted or substituted $C_{6-40}$ aryl; wherein when x is 1, the two groups $R^2$ are optionally directly covalently linked to each other;
X is —O—C(O)—CH$_2$—O— at each occurrence; and
$Z^-$ is an organic sulfonate anion.

9. The photoresist composition of claim 6,
wherein the photoacid generator compound of has one of formulae (2a), (2b), and (2c)

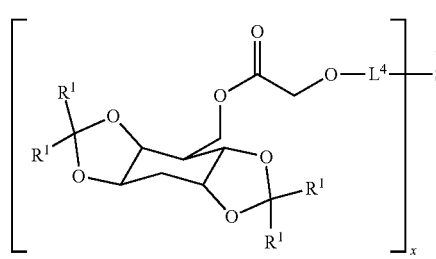
(2a)

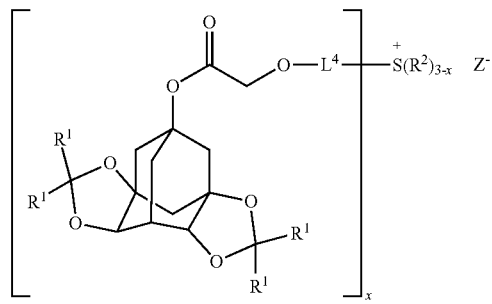

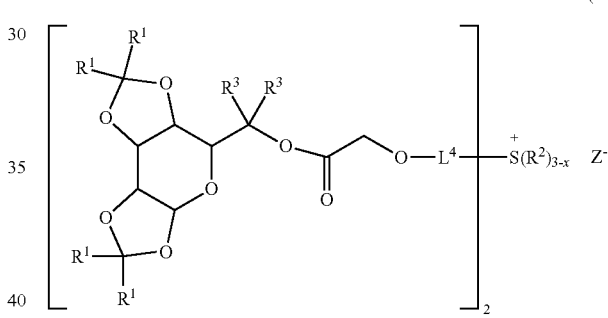

wherein
$R^3$ is independently at each occurrence hydrogen, an unsubstituted or substituted $C_{1-30}$ linear or branched alkyl, an unsubstituted or substituted $C_{3-30}$ cycloalkyl, an unsubstituted or substituted $C_{6-30}$ aryl, or an unsubstituted or substituted $C_{3-30}$ heteroaryl; wherein each occurrence of $R^3$ is optionally covalently linked to an adjacent occurrence of $R^3$; and
x, $L^4$, $R^1$, $R^2$, and $Z^-$ are defined as in claim 1.

10. The photoresist composition of claim 6,
wherein the photoacid generator compound of has one of formulae (4a), (4b), (4c), (4d), (4e), and (4f),

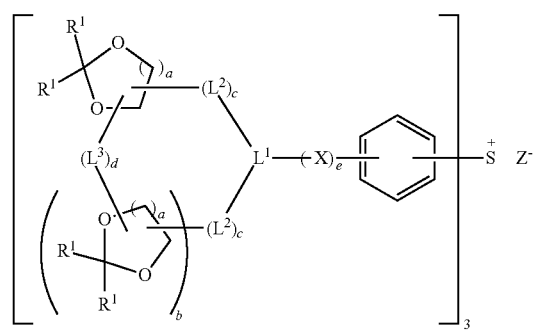
(4a)

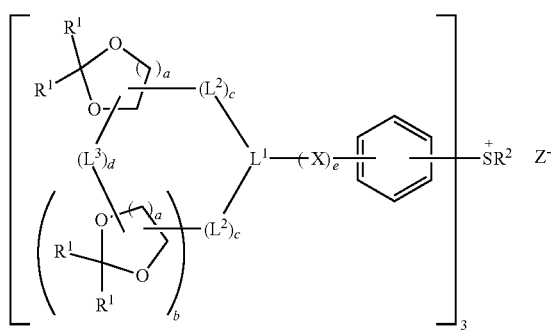
(4b)
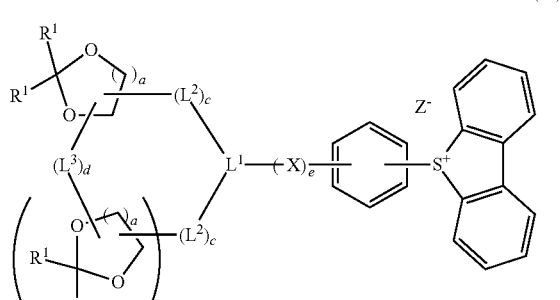
(4e)
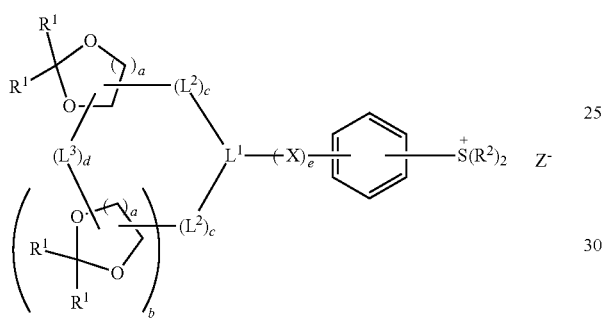
(4c)
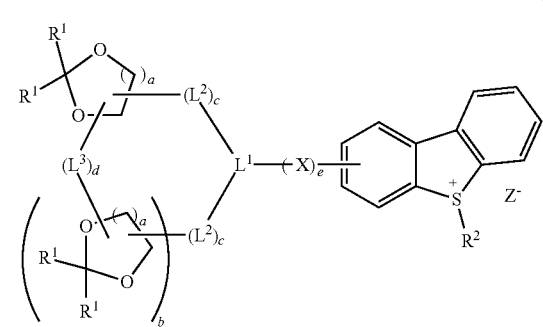
(4d)
(4f)
wherein a, b, c, d, e, $L^1$, $L^2$, $L^3$, $R^1$, $R^2$, X, and $Z^-$ are defined as in claim 1.
11. The photoresist composition of claim 6, wherein the photoacid generator compound of is selected from
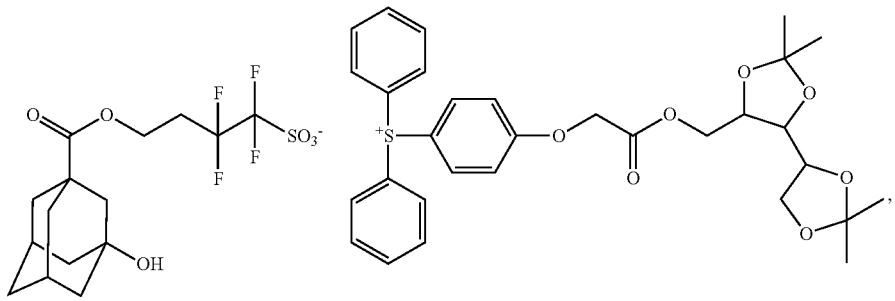

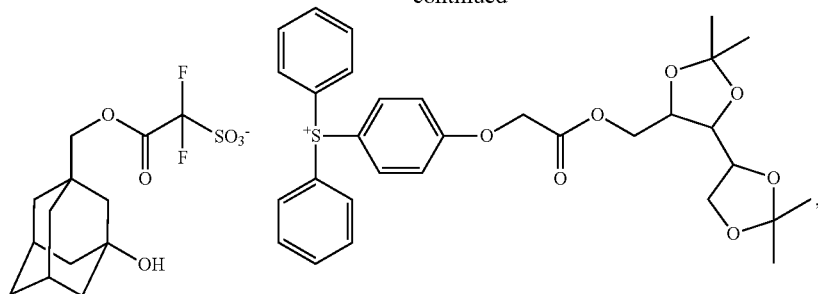

and combinations thereof.

12. The method of claim 7,
wherein
a is 1 at each occurrence;
b is 1;
c and d are as defined in claim 1;
e is 1;
x is 1;
$L^1$ and $L^3$ are each independently at each occurrence a single bond, or an unsubstituted or substituted $C_{1-20}$ aliphatic group; wherein $L^1$ and $L^3$ are optionally directly covalently linked;
$L^2$ is as defined in claim 1;
$L^4$ is at each occurrence an unsubstituted or substituted $C_{6-20}$ arylene;
$R^1$ is independently at each occurrence hydrogen, an unsubstituted $C_{1-12}$ linear or branched alkyl, an unsubstituted $C_{3-12}$ cycloalkyl, or an unsubstituted or substituted $C_{6-12}$ aryl;
$R^2$ is independently at each occurrence an unsubstituted or substituted $C_{6-40}$ aryl; wherein when x is 1, the two groups $R^2$ are optionally directly covalently linked to each other;
X is —O—C(O)—CH$_2$—O— at each occurrence; and
$Z^-$ is an organic sulfonate anion.

13. The method of claim 7,
wherein the photoacid generator compound of has one of formulae (2a), (2b), and (2c)

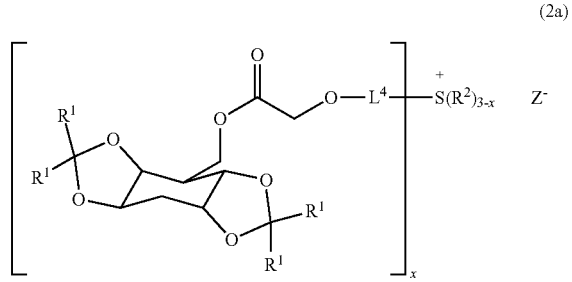 (2a)

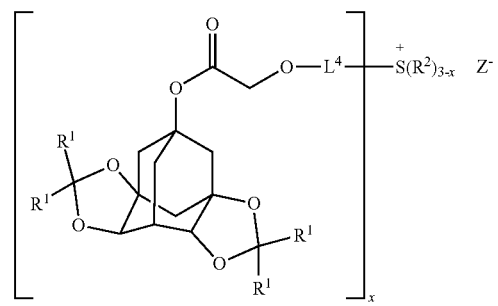 (2b)

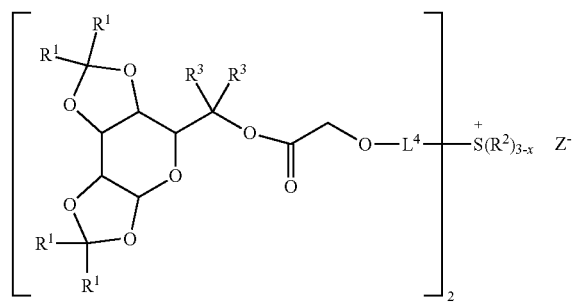 (2c)

wherein
$R^3$ is independently at each occurrence hydrogen, an unsubstituted or substituted $C_{1-30}$ linear or branched alkyl, an unsubstituted or substituted $C_{3-30}$ cycloalkyl, an unsubstituted or substituted $C_{6-30}$ aryl, or an unsubstituted or substituted $C_{3-30}$ heteroaryl; wherein each occurrence of $R^3$ is optionally covalently linked to an adjacent occurrence of $R^3$; and
x, $L^4$, $R^1$, $R^2$, and $Z^-$ are defined as in claim 1.

14. The method of claim 7,
wherein the photoacid generator compound of has one of formulae (4a), (4b), (4c), (4d), (4e), and (4f),

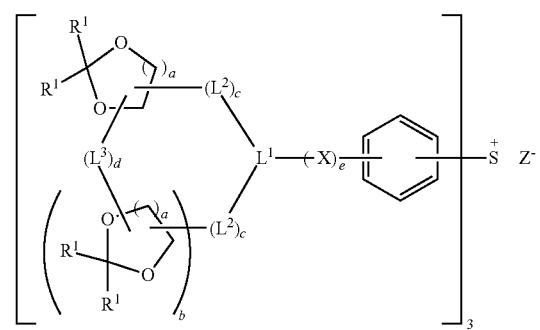 (4a)

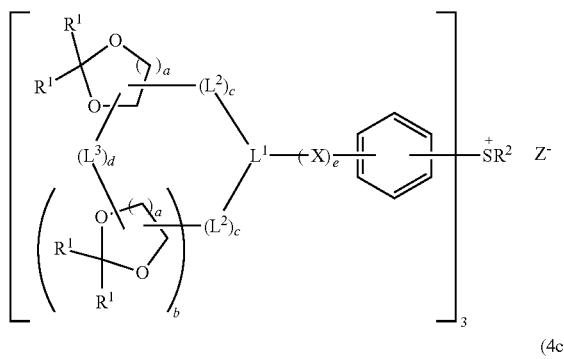
(4b)
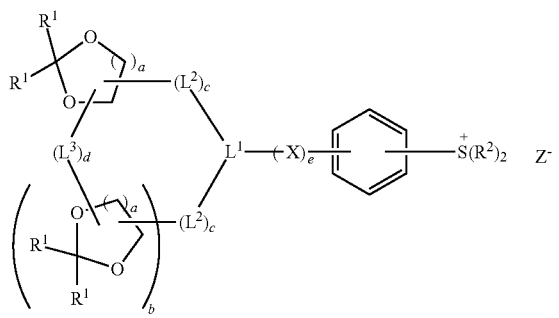
(4c)
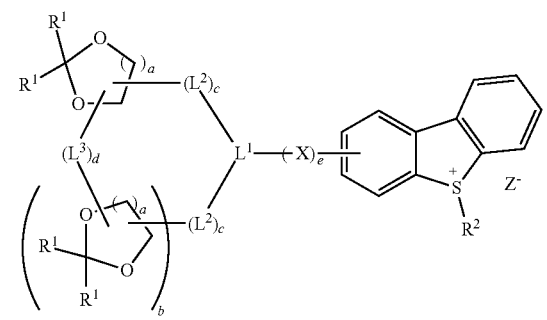
(4d)
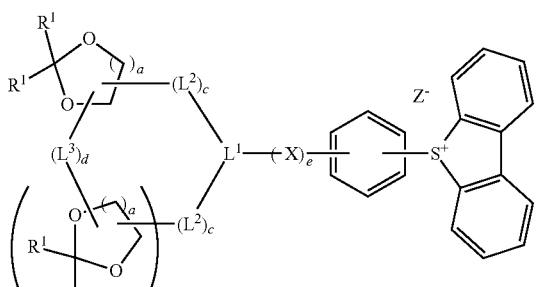
(4e)
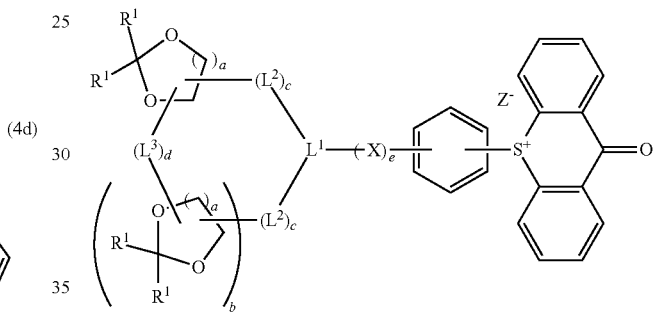
(4f)
wherein a, b, c, d, e, $L^1$, $L^2$, $L^3$, $R^1$, $R^2$, X, and $Z^-$ are defined as in claim 1.
15. The method of claim 7,
wherein the photoacid generator compound of is selected from
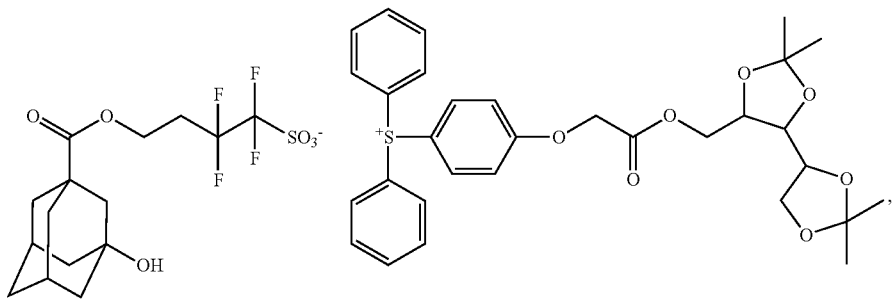

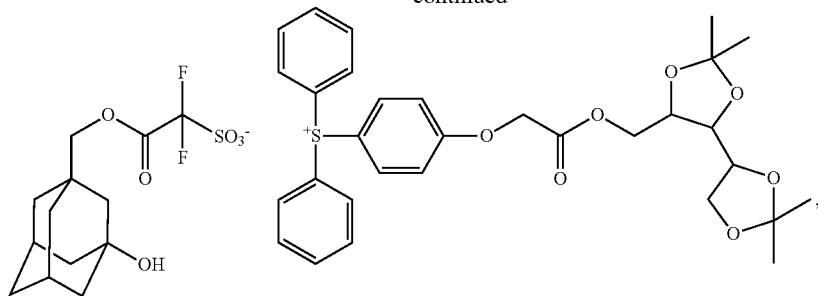

and combinations thereof.

16. A photoacid generator compound, having one of formulae (3a) and (3b)

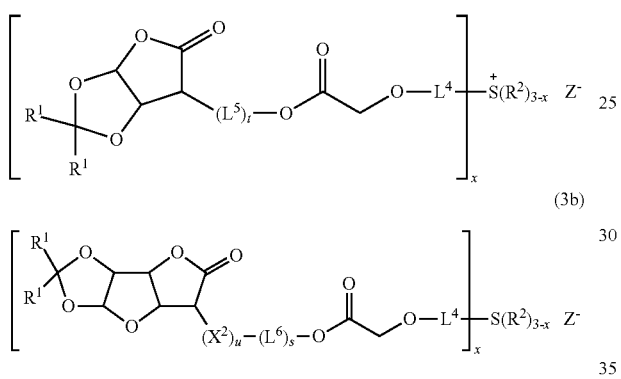

wherein
s is 0 or 1;
t is 0 or 1;
u is 0 or 1;
$L^5$ and $L^6$ are each independently at each occurrence an unsubstituted or substituted $C_{1-20}$ linear or branched alkylene, an unsubstituted or substituted $C_{3-20}$ cycloalkylene, or an unsubstituted or substituted $C_{6-20}$ arylene;
$X^2$ is independently at each occurrence —O— or —N(R)—, wherein R is hydrogen or $C_{1-6}$ alkyl;
x is 1;
$L^4$ is at each occurrence an unsubstituted or substituted $C_{6-20}$ arylene;
$R^1$ is independently at each occurrence hydrogen, an unsubstituted or substituted $C_{1-30}$ linear or branched alkyl, an unsubstituted or substituted $C_{3-30}$ cycloalkyl, an unsubstituted or substituted $C_{6-30}$ aryl, or an unsubstituted or substituted $C_{3-30}$ heteroaryl; wherein each occurrence of $R^1$ is optionally covalently linked to an adjacent occurrence of $R^1$; and wherein one or more occurrences of $R^1$ are optionally substituted with a polymerizable group;
$R^2$ is independently at each occurrence an unsubstituted or substituted $C_{6-40}$ aryl, an unsubstituted or substituted $C_{3-40}$ heteroaryl, an unsubstituted or substituted $C_{1-40}$ alkyl, or an unsubstituted or substituted $C_{3-4}$ cycloalkyl; wherein when x is 1, two groups $R^2$ are optionally directly covalently linked to each other; and wherein one or more occurrences of $R^2$ are optionally substituted with a polymerizable group; and $Z^-$ is an organic anion; wherein $Z^-$ is optionally substituted with a polymerizable group.

17. A photoresist composition comprising an acid-sensitive polymer and the photoacid generator compound of claim 16.

18. A polymer comprising a unit formed from a photoacid generator compound having formula (1)

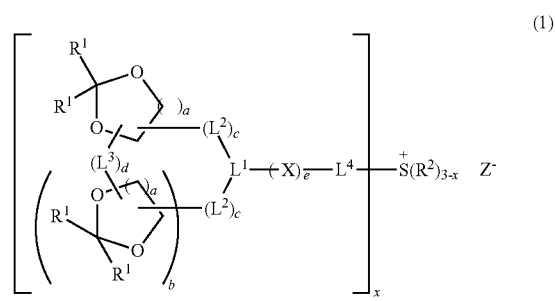

wherein
a is independently at each occurrence 0, 1, 2, 3, 4, 5, 6, 7, 8, 9, 10, 11, or 12;
b is independently at each occurrence 1, 2, 3, 4, or 5;
c is independently at each occurrence 0 or 1;
d is 0 or 1;
e is 1;
x is 1, 2, or 3;
$L^1$ and $L^3$ are each independently at each occurrence a single bond, an unsubstituted or substituted $C_{1-20}$ aliphatic group, an unsubstituted or substituted $C_{6-20}$ aromatic group, or an unsubstituted or substituted $C_{3-20}$ heteroaromatic group; wherein $L^1$ and $L^3$ are optionally directly covalently linked; and wherein one or more of $L^1$ and $L^3$ are optionally substituted with a polymerizable group;
$L^2$ is independently at each occurrence a single bond, a carbonyl group, an ester group, an amide group, an ether oxygen, or a $C_{1-20}$ aliphatic group optionally substituted with an ether oxygen, a carbonyl group, an ester group, an ether oxygen, or a combination thereof; wherein two occurrences of $L^2$ are optionally directly covalently linked; and wherein one or more occurrences of $L^2$ are optionally substituted with a polymerizable group;
$L^4$ is independently at each occurrence an unsubstituted or substituted $C_{6-20}$ arylene, an unsubstituted or substituted $C_{3-20}$ heteroarylene, an unsubstituted or substituted $C_{1-20}$ linear or branched alkylene, or an unsubstituted or substituted $C_{3-20}$ cycloalkylene; wherein $L^4$ is optionally covalently linked to an occurrence of $R^2$; and wherein one or more occurrences of $L^4$ are optionally substituted with a polymerizable group;

$R^1$ is independently at each occurrence hydrogen, an unsubstituted or substituted $C_{1-30}$ linear or branched alkyl, an unsubstituted or substituted $C_{3-30}$ cycloalkyl, an unsubstituted or substituted $C_{6-30}$ aryl, or an unsubstituted or substituted $C_{3-30}$ heteroaryl; wherein each occurrence of $R^1$ is optionally covalently linked to an adjacent occurrence of $R^1$; and wherein one or more occurrences of $R^1$ are optionally substituted with a polymerizable group;

$R^2$ is independently at each occurrence an unsubstituted or substituted $C_{6-40}$ aryl, an unsubstituted or substituted $C_{3-40}$ heteroaryl, an unsubstituted or substituted $C_{1-40}$ alkyl, or an unsubstituted or substituted $C_{3-40}$ cycloalkyl; wherein when x is 1, two groups $R^2$ are optionally directly covalently linked to each other; and wherein one or more occurrences of $R^2$ are optionally substituted with a polymerizable group;

X is independently at each occurrence an —O—, —S—, or an ether-, carbonyl-, ester-, carbonate-, amine-, amide-, urea-, sulfate-, sulfonate-, or sulfonamide-containing group, or combination thereof; wherein one or more occurrences of X are optionally substituted with a polymerizable group; and $Z^-$ is an organic anion; wherein $Z^-$ is optionally substituted with a polymerizable group.

19. A photoresist composition comprising a polymer of claim 18 and an acid-sensitive polymer, wherein the polymer of claim 18 and the acid-sensitive polymer are the same or different.

* * * * *